United States Patent
Abraham et al.

(10) Patent No.: US 11,648,310 B2
(45) Date of Patent: *May 16, 2023

(54) COMBINATION OF ANTI-FGFR4-ANTIBODY AND BILE ACID SEQUESTRANT

(71) Applicants: Daiichi Sankyo Europe GmbH, Munich (DE); Daiichi Sankyo Company Limited, Tokyo (JP)

(72) Inventors: Reimar Abraham, Munich (DE); Mauricio Redondo-Müller, Germering (DE)

(73) Assignee: BioInvent International AB

(*) Notice: Subject to any disclaimer, the term of this patent is extended or adjusted under 35 U.S.C. 154(b) by 182 days.

This patent is subject to a terminal disclaimer.

(21) Appl. No.: 16/935,582

(22) Filed: Jul. 22, 2020

(65) Prior Publication Data

US 2021/0023211 A1  Jan. 28, 2021

Related U.S. Application Data

(62) Division of application No. 15/575,255, filed as application No. PCT/EP2016/061131 on May 18, 2016, now Pat. No. 10,765,738.

(30) Foreign Application Priority Data

May 19, 2015 (EP) .................................... 15168152

(51) Int. Cl.

| *A61K 39/395* | (2006.01) |
| *A61K 31/07* | (2006.01) |
| *A61K 31/122* | (2006.01) |
| *A61K 31/355* | (2006.01) |
| *A61K 31/785* | (2006.01) |
| *A61K 45/06* | (2006.01) |
| *C07K 16/28* | (2006.01) |
| *A61P 35/00* | (2006.01) |
| *A61K 31/395* | (2006.01) |
| *A61K 39/00* | (2006.01) |
| *A61K 31/59* | (2006.01) |
| *A61K 31/787* | (2006.01) |
| *A61K 38/17* | (2006.01) |
| *A61P 21/00* | (2006.01) |
| *A61P 9/00* | (2006.01) |
| *A61P 3/04* | (2006.01) |
| *A61P 3/10* | (2006.01) |
| *A61P 13/12* | (2006.01) |

(52) U.S. Cl.

CPC .......... *A61K 39/3955* (2013.01); *A61K 31/07* (2013.01); *A61K 31/122* (2013.01); *A61K 31/355* (2013.01); *A61K 31/395* (2013.01); *A61K 31/59* (2013.01); *A61K 31/785* (2013.01); *A61K 31/787* (2013.01); *A61K 38/179* (2013.01); *A61K 39/395* (2013.01); *A61K 45/06* (2013.01); *A61P 3/04* (2018.01); *A61P 3/10* (2018.01); *A61P 9/00* (2018.01); *A61P 13/12* (2018.01); *A61P 21/00* (2018.01); *A61P 35/00* (2018.01); *C07K 16/2863* (2013.01); *A61K 2039/505* (2013.01); *A61K 2039/507* (2013.01); *A61K 2039/54* (2013.01); *A61K 2039/545* (2013.01); *C07K 2317/76* (2013.01)

(58) Field of Classification Search
CPC ................ A61K 39/3955; A61K 45/06; A61K 2039/505; A61K 2039/507; A61K 2039/54; A61K 2039/545; C07K 2317/76; C07K 16/2863; A61P 35/00

See application file for complete search history.

(56) References Cited

U.S. PATENT DOCUMENTS

2011/0150903 A1   6/2011   Baurin et al.

FOREIGN PATENT DOCUMENTS

| JP | 08208750 | 8/1996 |
| JP | H8-208750 | 8/1996 |
| JP | H8-208750 | 12/2019 |
| WO | 2012104654 A1 | 8/2012 |
| WO | 2016023894 | 2/2016 |
| WO | 2014160160 A2 | 12/2019 |

OTHER PUBLICATIONS

Hongfei Ge et al. "Fibroblast Growth Factor Receptor 4 (FGFR4) Deficiency Improves Insulin Resistance and Glucose Metabolism under Diet-Induced Obesity Conditions", Jrnl. Bio. Chem., vol. 289, No. 44, Oct. 2014, pp. 30470-30480.

Xing Xian Yu et al., peripheral Reduction of FGFR4 with Antisense Oligonucleotides Increases Metabolic Rate and Lowers Adiposity in Diet-Inductedd Obese Mice; PLOS One, vol. 8, No. 7, Jul. 2013, pp. e66923.

2017-557187 Japanese Office Action, dated Dec. 23, 2019.

EP15/168152.5, Extended European Search Report, dated Oct. 16, 2015.

PCT/EP2016/091131, International Search Report, dated Sep. 2, 2016.

Chen, Chaoyuan, Generation and Characterization of a Panel of Monoclonal Antibodies Specific for Human Fibroblast Growth Factor Receptor 4 (FGFR4), Hybridoma, 2005, pp. 152-159, vol. 24, No. 3 Mary Ann Liebert, Inc . . . .

French, Dorothy M., Targeting FGFR4 Inhibits Hepatocellular Carcinoma in Clinical Mouse Models, PLos ONE, www.plosone.org, May 2012, pp. 1-12, vol. 5 Issue 5.

(Continued)

*Primary Examiner* — Ruixiang Li
(74) *Attorney, Agent, or Firm* — Withers & Keys, LLC

(57) ABSTRACT

The present invention relates to the amelioration of toxic effects that are caused by therapies aimed at FGFR4-inhibition. In particular, the invention relates to the combination of FGFR4 inhibitors and agents capable of reducing bile acid levels and to the use thereof in the treatment of diseases.

5 Claims, 12 Drawing Sheets

Figure 1:
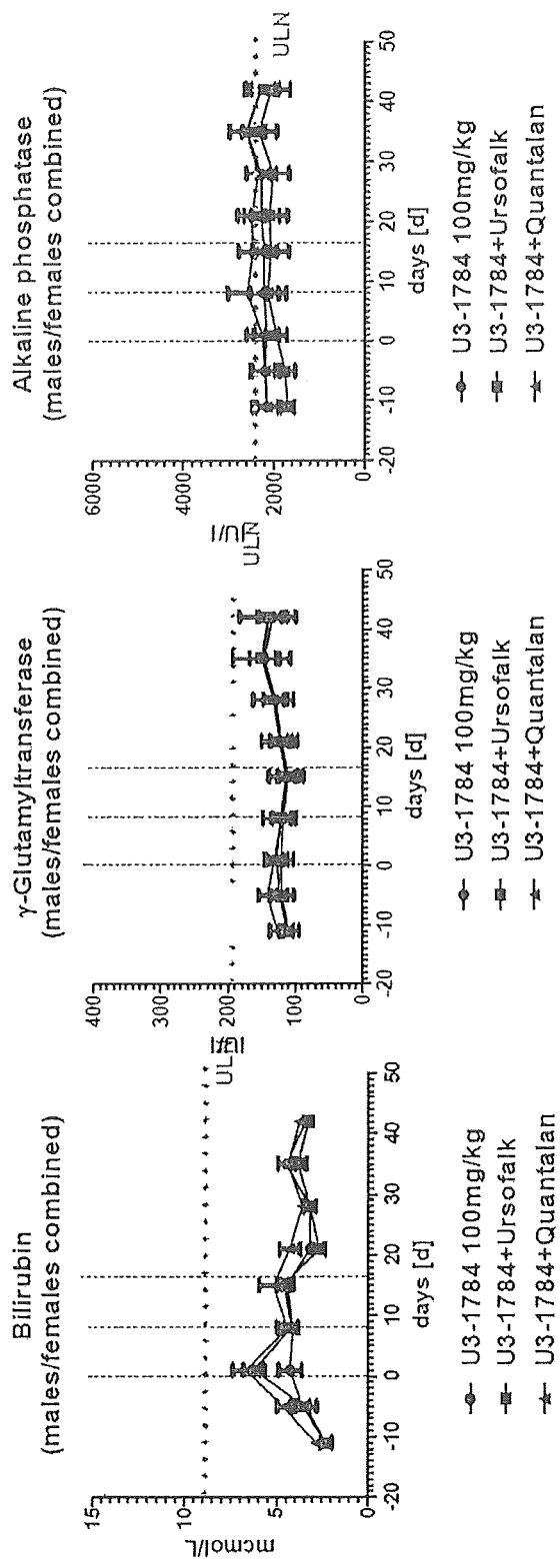

Specification includes a Sequence Listing.

(56) References Cited

OTHER PUBLICATIONS

Elshorst, Bettina, 1H, 13C and 15N assignment of D2 domain of human fibroblast growth factor receptor 4, Biomol NMR Assign, 2013, pp. 179-182, vol. 7, Springer Science+Business Media B.V.
Mellor, Howard R. Targeted inhibition of the FGF19-FGFR4 pathway in hepatocellular carcinoma; translational safety considerations, Liver International, 2014, pp. e1-e9, ISSN 1478-3223, John Wiley & Sons ltd.
Neuberger et al., Antibody Mediated Hepatocyte Injury in Methyl Dopa Induced Hepatotoxicity, Giu vol. 26 pp. 1233-1239, 1985.
Yamagiwa et al., Presence of Antiobodies Against Self Human Leukocyte Antigen Class II Molecules in Autoimmune Hepatitis, International Jrnl Medical Sciences, vol. 11, No. 9, pp. 850-856, 2014.
Walters et al., Managing Bile Acid Diarrhoea, Therapeutic Adv. In Gastroenterology, vol. 6, pp. 3649-357, 2010.
French, Dorothy M. et al., Targeting FGFR4 Inhibits Hepatocellular Carcinoma in Preclinical Mouse Models, PLoS ONE, www.plosone.org, May 2012, pp. 1-12, vol. 7, Issue 5.

COMBINATION OF ANTI-FGFR4-ANTIBODY AND BILE ACID SEQUESTRANT

This patent application is a divisional patent application of pending U.S. Utility patent application Ser. No. 15/575,255 entitled "COMBINATION OF ANTI-FGFR4-ANTIBODY AND BILE ACID SEQUESTRANT," filed on Nov. 17, 2017, which claims the benefit of priority to International Patent Application No. PCT/EP2016/061131, filed on May 18, 2016, which claims priority to European Patent Application Serial No. 15168152.5, filed on May 19, 2015, and entitled "COMBINATION OF ANTI-FGFR4-ANTIBODY AND BILE ACID SEQUESTRANT," the content of all of which is incorporated herein by reference in its entirety.

The present invention relates to the amelioration of toxic effects that are caused by therapies aimed at FGFR4-inhibition. In particular, the invention relates to the combination of FGFR4 inhibitors and agents capable of reducing bile acid levels and to the use thereof in the treatment of diseases.

Soluble fibroblast growth-factors (FGF) and their transmembrane receptors are involved in a broad range of cellular functions including proliferation, migration, differentiation and survival. Four of the receptors FGF1-4 possess tyrosine kinase domains and are activated by the binding of one 18 secreted glycoprotein FGFs to their extracellular immunoglobulin domains. Ligan-binding results in FGFR dimerization, auto-phosphorylation of the intracellular split tyrosine kinase domain and activation of downstream signalling pathways, such as the RAS-dependent nitrogen-activated protein kinase (MAPK) pathway, AKT-dependent anti-apoptotic pathway and signal transducer and activator of transcription (STAT) signalling.

FGFR4 (SEQ ID NO: 70) has been found to be of importance in a number of tumor types, with overexpression occurring in prostate, breast, pancreatic, pituitary, hepatocellular and gynecological tumors. FGFR4 has been recognized as an oncogene in breast cancer cell lines. In other tumor types, FGFR4 mutations are infrequent, but the single nucleotide polymorphism FGFR4 G388R increases stability, prolongs activation of the receptor and is associated with a poor prognosis in melanoma, breast, prostate and head and neck cancers. Considering the role of FGFR4 in a variety of tumor diseases, inhibition of FGFR4 is being extensively tested at the moment as a possible strategy for the treatment of hyperproliferative disorders.

Moreover, the inhibition of FGFR4 is expected to be successful for the treatment of further diseases, in particular cardiovascular diseases, such as hypertension, left ventricular hypertrophy (Faul et al, *J Clin Unvest,* 2011; 121(11): 4393-4408), chronic kidney disease (*Jimbo and Shimosawa, Int. J Hypertension,* 2014), muscular dystrophy (Zhao et al; 2006, *The Journal of Biological Chemistry,* 281, 429-438) and metabolic disease, in particular obesity or diabetes (Yu et al; 2013, PLos ONE, 8(7): e66923).

In addition to playing a part in the development of tumors and other diseases, FGFR4 plays an important homeostatic, physiological role in the regulation of bile acid homeostasis. FGF15/19 signalling via FGFR4 suppresses de novo bile acid production in the liver, tightly maintaining hepatic and systemic levels of these detergent-like molecules at a physiological threshold. This prevents pathological complications of raised bile acid levels such as colestatic liver injury and bile acid diarrhea.

No specific FGFR4 directed therapies have been tested in human to date and there was no data available on direct FGFR4 inhibition and its side effects in monkeys. From mouse experiments, it was known that FGFR4 activation in the liver by one of its ligands FGF19 leads to reduced expression of the enzyme that catalyzes the rate-limiting step of bile acid synthesis in hepatocytes—Cyp7A1 (Inagaki et al. (2005), Cell Metab. 2, 217-225). This therefore leads in turn to the repression of bile acid synthesis. FGFR4 knock-out mice are characterized by a small, depleted gallbladder and a two- to three-fold increase in secreted bile acids, relative to wildtype animals (Yu, C., et al. (2000), J. Biol. Chem. 275, 15482-9), whereas no toxic effect was apparent. In cynomolgus monkeys, an antibody against FGF19 was tested and found to induce heavy diarrhea and body weight loss caused by increased bile acid levels. All animals that were dosed with more than 3 mg/kg of the antibody had to be sacrificed (Pai et al.,2012, Toxicol. Sci. 126, 446-456). Antibody-mediated inhibition of fibroblast growth factor 19 resulted in increased bile acids synthesis and illegal malabsorption of bile acids in cynomolgus monkeys. Bile acids are carcinogens (Jansen P L, *J Hepatol* 2007; 47; 434-5) and dysregulation of bile acids is known to contribute to the development of hepatocellular carcinoma.

In a recent review article (Mellor H. R. 2014, Liver Int., 2014, 1-9), possible pathophysiological consequences of FGF19-FGFR4 blockade in patients with hepatocellular carcinoma are discussed. The authors conclude that it is unlikely to be possible to inhibit the FGF19-FGFR14 axis in the liver of hepatocellular carcinoma patients sufficiently to positively impact the malignancy without also triggering the dose limiting toxicities observed in primates treated with anti-FGF19. For relieving symptoms of diarrhea observed in patients affected with bile acid malabsorption, administration of bile acid sequestrants is mentioned. Due to expected side effects, such as, e.g., an adverse impact of bile acid sequestrant co-medications on gastrointestinal absorption and systemic exposure of orally administered FGF19-FGFR4 targeting, small molecule lipophilic compounds, the authors are critical about this approach. The prior art fails to provide a generally applicable strategy how to mitigate the toxic effects observed due to high bile acid levels and, at the same time, effectively inhibit the FGFR4 signaling pathway.

In the present invention it was surprisingly found out that toxic side effects afforded by inhibition of fibroblast growth-factor receptor 4 (FGFR4) through an FGFR4 inhibitor, can be prevented or treated if the FGFR4 inhibitor is combined with an additional active agent which is capable of reducing bile acid levels. It was observed that due to the biological function of FGFR4 in decreasing bile acid levels, inhibition of this receptor leads to increased bile acid levels which then lead to toxic effects on intestine and liver. Thus, the build-up of bile acid levels can be prevented according to the present invention by binding bile acids in the intestine by means of bile acid sequestrants which are subsequently excreted along with the bound bile acids. Concurrently, the desired activity of the co-medicated FGFR4 inhibitors is not impaired. This approach makes it possible to use FGFR4-directed therapies without observing excessively toxic side effects which may prevent a successful treatment of patients.

A first aspect of the present invention refers to an FGFR4 inhibitor in combination with an an agent capable of reducing bile acid levels, for use in the prevention, alleviation Orland treatment of diseases, in particular dise associated with FGFR4 expression, overexpression and/or hyperactivity.

The diseases to be treated are in particular hyperproliferative disorders, cardiovascular diseases, in particular hypertension, left ventricular hypertrophy, heart hypertrophy, chronic kidney diseases, muscular dystrophy and metabolic diseases, in particular obesity and diabetes.

A "hyperproliferative disease" or "hyperproliferative disorder" as used herein includes any neoplasia, i.e. any abnormal new growth of tissue in animals which may depend upon a dysfunction or/and a loss of growth regulation. A hyperproliferative disorder includes tumour diseases and/or cancer, e.g. solid tumors such as carcinomas, adenomas and sarcomas or non-solid tumors such as leukemias. The hyperproliferative disorder is preferably characterized by FGFR4 overexpression, i.e. an increased FGFR4 expression compared to normal tissue.

In the present invention, the hyperproliferative disorder is preferably cancer, more preferably the hyperproliferative disorder is selected from hepatocellular carcinoma, rhabdomyosarcoma, soft tissue sarcoma, head and neck squamous carcinoma, lung adenocarcinoma, kidney cancer, bladder cancer, brain cancer, esophagus cancer, gastric cancer, pancreas cancer, small intestine cancer, colon cancer, breast cancer, lung cancer, liver cancer, spleen cancer, thyroid cancer, pituitary cancer, adrenal cancer, ovarian cancer, cervix cancer, testis cancer, prostate cancer, glioma, melanoma, or/and leukemia, in particular hepatocellular carcinoma, In a preferred embodiment, the cancer is a non-metastatic cancer, particularly a non-metastatic cancer in patients having the FGFR4-388Gly allele or/and the FGFR4-388Arg allele. In a further embodiment, the cancer is a metastatic cancer, particularly a metastatic cancer in patients having the FGFR4-388 Arg allele.

In case of a metastatic cancer, the invention is suitable for the treatment of metastases, metastases formation or/and metastases progression, in particular in micrometastases, preferably in the hyperproliferative disorders as defined above. Metastases, in particular micrometastases, are often not accessible by surgery and need pharmacological or/and irradiation treatment.

According to another embodiment, the disease associated with FGFR4 expression, overexpression and/or hyperactivity is a metabolic disease, in particular metabolic syndrome or obesity.

According to a still further embodiment of the invention, the disease associated with FGFR4 expression, overexpression and/or hyperactivity is ventricular hypertrophy, heart hypertrophy or chronic kidney disease.

The agent capable of reducing bile acid levels to be combined with the FGFR4 inhibitor of the present invention is preferably a bile acid sequestrant such as colestyramine, colestipol and/or colesevelam. Agents capable of promoting clearance of bile acids, such as ursodeoxycholic acid were surprisingly found to be less suitable for the purpose of the present invention. According to a particularly preferred aspect of the invention, the agent capable of reducing bile acid levels is a bile acid sequestrant, in particular colestyramine. It was surprisingly found that colestyramine is superior to other bile acid sequestrants and agents capable of promoting clearance of bile acids. It is particularly suitable to trigger the toxicities caused by FGFR4 inhibitors, while it does not adversely impact the desired activity of inhibiting the FGFR4 signaling pathway.

The invention also encompasses the administration of at least two agents capable of reducing bile acid levels as defined in above. In particular, two, three, four or five agents capable of reducing bile acid levels. In particular, two or more bile acid sequestrants can be combined.

Using colestyramine as the agent capable of reducing bile acid levels, it was found that an amount of 0.1 to tog per kilogram bodyweight per day is a particularly suitable dose when combined with an inhibitor of FGFR4.

Preferably, 0.2 to 0.6 g per kilogram bodyweight per day, in particular 0.3 to 0.4 g per kilogram bodyweight per day, for example about 0.35 g per kilogram bodyweight per day, were found to be suitable.

Co-administration (also termed combination treatment or combination therapy) as used herein refers to the administration of an FGFR4 inhibitor of the present invention and an agent capable of reducing bile acid levels, so that they are active at the same time.

Co-administration includes the administration of the FGFR4 inhibitor and the agent capable of reducing bile acid levels (e.g. one or more bile acid sequestrants) in the form of a single composition or in the form of distinct compositions, preferably at least two distinct compositions, more preferably two distinct compositions. Co-administration includes the administration of the agent capable of reducing bile acid levels (in particular one or more bile acid sequestrants) and the FGFR4 inhibitor simultaneously (i.e. at the same time) or sequentially, i.e. at intervals.

Co-administration "at intervals" includes the administration of the agent capable of reducing bile acid levels (in particular one or more bile acid sequestrants) and the FGFR4 inhibitor within an interval of 1 h at the maximum, 6 h at the maximum, 12 h at the maximum, 1 day at the maximum or 1 month at the maximum. Co-administration at intervals also includes the administration of the agent capable of reducing bile acid levels (in particular one or more bile acid sequestrants) and the FGFR4 inhibitor with the same or with different schedules on a daily, weekly or monthly basis, which may also depend on the dosage forms of the agent capable of reducing bile acid levels and the FGFR4 inhibitor, which may be identical or different, e.g. fast release dosage forms, controlled release dosage forms or/and depot forms. For example, co-administration includes different schedules for administration of the agent capable of reducing bile acid levels (in particular one or more bile acid sequestrants) and the FGFR4 inhibitor.

The agent capable of reducing bite acid levels (in particular one or more bile acid sequestrants) and the FGFR4 inhibitor may be administered together or separately. It is particularly preferred to administer the FGFR4 inhibitor and the agent capable of reducing acid levels (in particular one or more bile acid sequestrants) separately as two distinct compositions. It is possible to administer the FGFR4 inhibitor and the agent capable of reducing bile acid levels (in particular one or more bile acid sequestrants) in a single dose or divided in two or more, in particular two or three doses per day. For the FGFR4 inhibitor it is preferred to administer a single dose per day. For the agent capable of reducing bile acid levels, two or three doses per day are particularly preferred.

In one embodiment of the present invention, the FGFR4 inhibition is a specific inhibition. "Specific inhibition" is a selective inhibition of the FGFR4 activity. In a specific inhibition of FGFR4, the activity of other cellular components, in particular receptors (such as FGFR1, FGFR2 or/and FGFR3) is not significantly inhibited, i.e. the 1050 values of the specific FGFR4 inhibitor to other cellular components are at least a factor of 10, preferably a factor of 100, more preferably a factor of 1000 larger than the 1050 values to FGFR4. According to the present invention, it is preferred to use a specific FGFR4 inhibitor. Non-specific inhibition of FGFR4 is possible, but less preferred.

The FGFR4 inhibitor of the present invention is preferably a molecule specifically binding to the extracellular domain of FGFR4.

The FGFR4 inhibitor of the present invention may be a direct inhibitor or an indirect inhibitor, A direct inhibitor of FGFR4 directly inhibits FGFR4, an FGFR4 transcript or/and the FGFR4 gene, thereby reducing the FGFR4 activity.

An indirect FGFR4 inhibitor does not directly inhibit FGFR4 as described above, but acts on a target which interacts with FGFR4, e.g. an FGFR4 ligand, such as FGF1, -2, -4, -6, -8, -16, -17, -18 or -19, a downstream target, such as BclXL or a protein in the MAP kinase cascade, such as End or/and Erk2. Furthermore, an indirect inhibition of FGFR4 may be effected by transcriptional or translational inhibitors or inhibitors of transport ways or lipid rafts. "FGFR4 activity" as used herein includes the capability of an FGFR4 polypeptide to generate a physiological or pathophysiological effect, particularly a resistance of a cell against apoptosis.

In the present invention, the activity of FGFR4 may be inhibited on the nucleic acid level, e.g. on the gene level or on the transcription level. Inhibition on the gene level may comprise a partial or complete gene inactivation, e.g. by gene disruption. Inhibition may also occur on the transcript level, e.g. by administration of anti-sense molecules, ribozymes, siRNA molecules, which may be directed against FGFR4 mRNA, FGFR4 ligand mRNA or/and against mRNA of a downstream target. Suitable anti-sense molecules may be selected from DNA molecules, RNA molecules and nucleic acid analogues. Ribozymes may be selected from RNA molecules and nucleic acid analogues, Small double-stranded RNA molecules capable of RNA interference (siRNA molecules) may be selected from RNA molecules and nucleic acid analogues. Preferred double-stranded siRNA molecules have a strand length of 19-25 nucleotides and optionally at least one 3'-overhang. Suitable siRNA molecules may e.g. be obtained according to Elbashir et al. (Nature 411 (2001), 494-498), Elbashir et al. (Genes & Dev. 15 (2001), 188-200) or Elbashir et al. (EMBO J. 20 (2001), 6877-6898). The content of these documents is herein incorporated by reference.

Further, the FGFR4 activity may be inhibited on the protein level, e.g. by administration of compounds which result in a specific FGFR4 inhibition. The inhibition on the protein level may comprise, for example, the application of antibodies or antibody fragments. In particular, these antibodies or antibody fragments are specifically directed against FGFR4, preferably against the extracellular domain of FGFR4, or against FGFR4 Uganda or/and against downstream targets. The antibodies may be polyclonal antibodies c monoclonal antibodies, recombinant antibodies, e.g. single chain antibodies or fragments of such antibodies which contain at least one antigen-binding site, e.g. proteolytic antibody fragments such as Fab, Fab' or F(ab')2 fragments or recombinant antibody fragments such as scFv fragments. For therapeutic purposes, particularly for the treatment of humans, the administration of chimeric antibodies, humanized antibodies or human antibodies is especially preferred.

Exemplary, anti-FGFR4 antibodies that can be used according to the present invention are described, e.g., in WO 2014/105849, WO 2012/138975 and WO 2010/004204.

According to a particularly preferred embodiment of the invention, the FG R4 inhibitor is a human anti-FGFR4 antibody. The term "human antibody" encompasses fully human or humanized antibodies, wherein fully human antibodies are preferred. Human antibodies may be prepared from genetically engineered animals, e.g. animals comprising a xenogenic immune system or from antibody display libraries according to known techniques. Human antibodies are described generally in van Dijk and van de Winkel (Curr. Opin. Pharmacol. 5: 368-74 (2001)) and Lonberg (Curr. Opin. Irnmunol. 20: 450-459 (2008)). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see for example Lonberg, Nat. Biotech. 23: 1117-1125 (2005). Human variable regions from intact antibodies generated by such animals may be further modified, e.g. by combining with a different human constant region.

Human antibodies can also be made by hybridoma-based methods. Human myeloma and mouse-human heteromyeloma cell lines for the production of human monoclonal antibodies have been described (see e.g. Kozbor J, mmunol. 133: 3001 (1984); Brodeur et al., Monoclonal Antibody Production Techniques and Applications, pp. 51-63). Human antibodies generated via human B-cell hybridoma technology are also described in Li et al, Proc. Natl. Acad. Sci USA 103: 3557-3562 (2006).

Human antibodies may also be generated by phage display methods (see e.g., U.S. Pat. Nos. 6,248,516, 5,403,484, 5,969,108, 5,885,793, 6,696,248, 5,849,500). Techniques for selecting human antibodies from antibody libraries are known in the art (see e.g., Carmen, S. et al., Briefings in Functional Genomics and Proteomics (2002), 1 (2), p. 189-203; and Siriwardena, D. et al., Ophthalmology (2002) 109 (3), p. 427-431), For example, a phage display method can be used, which involves causing human antibody variable regions to be expressed as a single-chain antibody (scFv) on phage surface and selecting phages binding to antigens (Nature (1991), 352, (6336), p. 624-628, Journal of Molecular Biology (1992), 227, (2), p 381-388, and Nature Biotechnology (2005), 23, (9), p. 1105-1116). Likewise, another phage display method can also be used, which involves causing human antibody Fab (antigen-binding fragment) to be expressed on the surface of phage and selecting phages binding to antigens MO 97/08320 and WO 01/05950). Genes of the phages selected based on antigen binding can be analyzed to thereby determine DNA sequences encoding human antibody variable regions binding to the antigens. When the DNA sequence of scFv or Fab binding to the antigens is clarified, CDR sequences are extracted therefrom, and expression vectors having the sequences can be prepared and introduced into appropriate hosts, followed by gene expression to obtain human antibodies (WO 92/01047, WO 92/20791, WO 93/06213, WO 93/11236, WO 93/19172, WO 95/01438, WO 95/15388, Annu. Rev. Immunol (1994) 12, p. 433.455, and Nature Biotechnology (2005) 23 (9), p. 1105-1116).

Human antibodies may also be generated by isolating Fv clone variable domain sequences selected from human-derived phage display libraries. Such variable domain sequences may then be combined with a desired human constant domain, Techniques for selecting human antibodies from antibody libraries are known in the art.

Humanized antibodies may be prepared by humanization of monoclonal antibodies according to known techniques.

Typically, a non-human antibody is humanized to reduce immunogenicity to humans, while retaining the specificity and affinity of the parental non-human antibody. Humanized antibodies and methods of making them are reviewed, e.g. in Alamagro and Fransson, Front. Biosci. 13: 1619-1633 (2008). It is also possible to use fragments of human antibodies, e.g., portions of the above-mentioned antibodies which comprise at least one antigen binding site. Examples of antibody fragments include Fab fragments, Fab' fragments, F(ab')2 fragments, Fv fragments, diabodies or single chain antibody molecules and other fragments as long as they exhibit the desired capability of binding to human FGFR4. For a review of certain antibody fragments see Hudson et al., Nat. Met. 9: 129-134 (2003).

Diabodies are antibody fragments with two antigen binding sites that may be bivalent or bispecific. See for example Hudson et al., (2003). Single-chain antibodies are antibody fragments comprising all or a portion of the heavy chain variable domain or all, or a portion of the light chain variable domain of an antibody. Antibody fragments can be made by various techniques including but not limited to proteolytic digestion of an intact antibody as well as production by recombinant hosts (e.g. E. coli or phage) as described herein.

In certain embodiments, an antibody used according to the present invention is a multi-specific antibody, e.g., a bispecific antibody. Multi-specific antibodies are monoclonal antibodies that have binding specificities for at least to different sites.

In certain embodiments, one of h binding specificities is for FGFR4 and the other is for any other antigen.

In certain embodiments, bispecific antibodies may bind to two different epitopes of FGFR4. Bispecific antibodies may also be used to localize cytotoxic agents to cells which express FGFR4. Bispecific antibodies can be prepared as full-length antibodies or antibody fragments.

Techniques for making multispecific antibodies include but are not limited to recombinant co-expression of two immunoglobulin heavy chain-light chain pairs having different specificities and "knob in hole" engineering. Multi-specific antibodies may also be made by engineering electrostatic steering effects for making antibody Fc-heterodimeric molecules; crosslinking two or more antibodies or fragments; using leucine zippers to produce bispecific antibodies; using "diabody" technology for making bispecific antibodies and using single-chain Fv and preparing trispecific antibodies as described. Engineered antibodies with three or more functional antigen binding sites including "octopus antibodies" are also included herein.

Particularly preferred for use in the present invention are antibodies directed against an epitope between amino acids 119-284 of human FGFR4 or functional fragments or functional derivatives thereof are particularly useful for therapeutic and diagnostic applications. Particularly preferred are human antibodies directed against an epitope between amino acids 152-240 and more preferably between amino acids 230 and 240 of human FGFR4. According to a particularly preferred embodiment, the antibody of the invention is directed against an epitope comprising, essentially consisting of or consisting of the amino acid sequence RYNY (SEQ ID NO: 69).

The epitope recognized by a human antibody of the invention is preferably located in the Hg-like domain 2 of human FGFR4.

The antibodies of the invention may be of various immunoglobulin (Hg) types, for example of the IgA-, IgD-, IgE-, IgG- or IgM-type, preferably of the IgG- or IgM-type including but not limited to the IgG1-, IgG2-, IgG3-, IgG4-, IgM1 and IgM2-type. In one preferred embodiment the antibody is of the IgG1type.

In certain embodiments of the present invention, the antibody may comprise specific heavy chain complementarity determining regions CDRH1, CDRH2 and/or CDRH3 as described herein below.

In one embodiment, the human an body comprises a heavy chain complementarity determining region 1 (CDRH1) having, the amino acid sequence as shown in any one of SEQ ID NOs: 1-6, or an amino acid sequence differing in 1 or 2 amino acids therefrom.

In a further embodiment, the antibody comprises a heavy chain cornplementarity determining region 2 (CDRH2) having the amino acid sequence as shown in any one of SEQ ID NOs: 7-12, or an amino acid sequence differing in 1 or 2 amino acids therefrom.

In yet a further embodiment, the antibody comprises a heavy chain complementarity determining region 3 (CDRH3) having the amino acid sequence as shown in any one of SEQ ID NOs: 13-20, or an amino acid sequence differing in 1 or 2 amino acids therefrom.

The antibody used according to the invention may also comprise specific light chain complementarity determining regions CDRL1, CDRL2 and/or CDRL3.

Accordingly, in one embodiment, the antibody comprises a light chain complementarity determining region 1 (CDMA) having the amino acid sequence as shown in any one of SEQ ID NOs: 21-23 and 68, or an amino acid sequence differing in 1 or 2 amino acids therefrom.

In a further embodiment, the antibody comprises a tight chain complementarity determining region 2 (CDRL2) having the amino acid sequence as shown in any one of SEQ ID NOs: 24-27, or an amino acid sequence differing in 1 or 2 amino acids therefrom.

In yet a further embodiment, the antibody comprises a light chain complementarity determining region 3 (CDRL3) having the amino acid sequence as shown in any one of SEC) ID NOs: 28-35, or an amino acid sequence differing in 1 or 2 amino acids therefrom.

The antibody for use in the present invention may preferably comprise a specific combination of CDRs (i.e. of CDRH1, CDRH2 and CORM) within one heavy chain.

Accordingly, in one preferred embodiment, the antibody comprises a heavy chain comprising complementarity determining regions CDRH1, CDRH2 and CDRH3, wherein CDRH1 is selected from the sequences as shown in SEQ ID NOs: 1-6, or an amino acid sequence differing in 1 or 2 amino acids therefrom, CDRH2 is selected from the sequences shown in SEQ ID NOs: 7-12, or an amino acid sequence differing in 1 or 2 amino acids therefrom, and CDRH3 is selected from the sequences shown in SEQ ID NOs: 13-20, or an amino acid sequence differing in 1 or 2 amino acids therefrom.

Most preferably, the antibody for use in the invention comprises a heavy chain comprising three CDRs, wherein the combination of CDRH1, CDRH2 and CDRH3 is selected from those shown in table 1. It is understood that each line of this table represents one specific combination of a CDRH1, a CDRH2 and a CDRH3.

TABLE 1

| CDRH1 | CDRH2 | CDRH3 |
|---|---|---|
| RNYMS (SEQ ID NO. 1) | AISGSGGSTYYADSVKG (SEQ ID NO. 7) | VTSPGAFDI (SEQ ID NO. 13) |

TABLE 1-continued

| CDRH1 | CDRH2 | CDRH3 |
|---|---|---|
| KAWMS (SEQ ID NO. 2) | AISGSGGSTYYADSVKG (SEQ ID NO. 7) | LYSYGDFDH (SEQ ID NO. 14) |
| DYYMS (SEQ ID NO. 3) | TISGSGGSTYYADSVKG (SEQ ID NO. 8) | LTAYGHVDS (SEQ ID NO. 15) |
| SNYMS (SEQ ID NO. 4) | LISGSGGSTYYADSVQG (SEQ ID NO. 9) | NTAGFGYFDL (SEQ ID NO. 16) |
| SNYMN (SEQ ID NO. 5) | VISYDGSNKYYADSVKG (SEQ ID NO. 10) | KSRDFWRGPFDY (SEQ ID NO. 17) |
| SNYMS (SEQ ID NO. 4) | SISGSGGRTYYADSVKG (SEQ ID NO. 11) | MTVFGAATL (SEQ ID NO. 18) |
| DYYMN (SEQ ID NO. 6) | AIGGSGDRTYYADSVKG (SEQ ID NO. 12) | GGSYFGY (SEQ ID NO. 19) |
| DYYMS (SEQ ID NO. 3) | AISGSGGSTYYADSVKG (SEQ ID NO. 7) | LATYGPFDD (SEQ ID NO. 20) |

According to the present invention, it is further preferred that the antibody comprises a specific combination of CDRs within one light chain (i.e. of CDRL1, CDRL2 and CDRL3).

Thus, in one preferred embodiment, the antibody comprises a light chain comprising complementarity determining regions CDRL1, CDRL2 and CDRL3, wherein CDRL1 has the amino acid sequence as shown in any of SEQ ID NOs: 21-23 and 68, or an amino acid sequence differing in 1 or 2 amino acids therefrom, CDRL2 has the amino acid sequence as shown in any of SEQ ID NOs: 24-27, or an amino acid sequence differing in 1 or 2 amino acids therefrom, and CDRL3 has the amino acid sequence as shown in any of SEQ ID NOs: 28-35, or an amino acid sequence differing in 1 or 2 amino acids therefrom.

Most preferably, the antibody of the invention comprises a light chain comprising three CDRs, wherein the combination of CDRL1, CDRL2 and CDRL3 is selected from those shown in table 2. It is understood that each line of this table represents one specific combination of a CDRL1, a CDRL2 and a CDRL3.

TABLE 2

| CDRL1 | CDRL2 | CDRL3 |
|---|---|---|
| SGGTSNIGTNTVN (SEQ ID NO. 21) | RNNQRPS (SEQ ID NO. 24) | AAWDDSLNGPYVV (SEQ ID NO. 28) |
| SGSSSNIGSNTVN (SEQ ID NO. 22) | RNNQRPS (SEQ ID NO. 24) | AAWDDSLNGPAVV (SEQ ID NO. 29) |
| SGSSSNIGTNTVN (SEQ ID NO. 23) | RNYQRPS (SEQ ID NO. 25) | AAWDDSLSGPHVV (SEQ ID NO. 30) |
| SGSSSNIGSNTVN (SEQ ID NO. 22) | RNNQRPS (SEQ ID NO. 24) | AAWDDSLNGPLVV (SEQ ID NO. 31) |
| SGSSSNIGSNTVN (SEQ ID NO. 22) | RNNQRPS (SEQ ID NO. 24) | STWDDSLRGWV (SEQ ID NO. 32) |
| SGSSSNIGSNTVN (SEQ ID NO. 22) | RNNQRPS (SEQ ID NO. 24) | AAWDDSLNGPYWV (SEQ ID NO. 33) |
| SGSSSNIGSNTVN (SEQ ID NO. 22) | YDDLLPS (SEQ ID NO. 26) | AAWDDSLNGPV (SEQ ID NO. 34) |

As described above, the complementarily determining regions (CDRs) of an antibody may be flanked by framework regions. A heavy or light chain of an antibody containing three CDRs contains e.g. four framework regions.

Additionally, the present invention also encompasses those antibodies that recognize the same epitope on human FGFR4 as a specific antibody characterized by the above heavy and/or light chain CDRs. Functional fragments and functional derivatives of those antibodies are also within the scope of the invention. To determine the epitope on FGFR4 recognized by the antibody, chemically prepared arrays of protein sequence derived short peptides derived from the amino acid sequence of the extracellular domain of human FGFR4 can be used to locate and identify antibody epitopes (Reinicke W., Methods Mol, Biol. 2004, 248: 443-63). A further method to map the epitopes in the FGFR4 extracellular domain bound by the antibodies of the invention comprises Snaps/SELDI (Wang et al, Int, J. Cancer, 2001, June 15; 92 (6): 871-6) or a routine cross-blocking assay such as described in Antibodies, A Laboratory Manual, Cold Spring Harbor Laboratory, Ed Harlow and David Lane (1988) can be performed.

According to a particularly preferred embodiment, the human antibody for use according to the invention comprises a heavy chain comprising at least one CDR selected from the group consisting of
  (a) a CDRH1 as shown in SEQ ID NO: 1-6, or a CDRH1 sequence differing in 1 or 2 amino acids therefrom,
  (b) a CDRH2 as shown in SEC) ID NO: 7-12, or a CDRH2 sequence differing in 1 or 2 amino acids therefrom, and
  (c) a CDRH3 as shown in SEQ ID NO: 13-20, or a CDRH3 sequence differing in 1 or 2 amino acids therefrom, and/or a light chain comprising at least one CDR selected from the group consisting of
  (d) a CDRL1 as shown in SEQ ID NO: 21-23 or 6 or a CDRL1 sequence differing in 1 or 2 amino acids therefrom,
  (e) a CDRL2 as shown in SEQ ID NO: 24-27, or a CDRL2 sequence differing in 1 or 2 amino acids therefrom, and a CDRL3 as shown in SEQ ID NO: 28-35, or a CORO sequence differing in 1 or 2 amino acids therefrom.

In a preferred embodiment of the invention, the human antibody comprises a heavy chain variable region (VH) as shown in any one of SEQ ID NOs, 52-59 or a sequence differing in 1 or 2 amino acids therefrom. Furthermore, the human antibody of the invention preferably comprises a light chain variable region (VL) as shown in any one of SEQ ID NOs. 60-67 or a sequence differing in 1 or 2 amino acids therefrom. Particularly preferred are human antibodies comprising a heavy chain variable region as shown in any one of SEQ ID NOs. 52-59 and a light chain variable region as shown in in any one of SEQ ID NOs. 60-67. In particular, it is preferred to use any one of antibodies U4-1 to U4-9 disclosed below.

Particularly preferred is a human antibody (U4-1) comprising a heavy chain comprising a CDRH1 as shown in SEQ ID NO: 1, a CDRH2 as shown in SEQ ID NO: 7 and a CDRH3 as shown in SEQ ID NO: 13 and a light chain comprising a CDRL1 as shown in SEQ ID NO: 21, a CDRL2 as shown in SEQ ID NO: 24 and a CDRL3 as shown in SEQ ID NO: 28, Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 52 and a light chain variable region according to SEQ ID NO: 60. Also suitable are human antibodies wherein the sequences of the variable region of the heavy chain and/or the light chain differ in 1 or 2 amino acids from those shown in SEQ ID NOs. 52 and 60.

Particularly preferred is a human antibody (U4-2) comprising a heavy chain comprising a CDRH1 as shown in SEQ ID NO: 2, a CDRH2 as shown in SEQ ID NO: 7 and a CDRH3 as shown in SEQ ID NO: 14 and a light chain comprising a CDRL1 as shown in SEQ ID NO: 22, a CDRL2 as shown in SEQ ID NO: 24 and a CDRL3 as shown in SEQ ID NO: 29. Also suitable are human antibodies, wherein one or more of the CDRs differ in 1 or 2 amino acids or antibodies recognizing the same epitope on human FGFR4: In a particularly preferred embodiment, the human antibody comprises a heavy chain variable region according to SEQ ID NO: 53 and a light chain variable region according to SEQ ID NO: 61. Also suitable are human antibodies wherein the sequences of the variable region of the heavy chain and/or the light chain differ in 1 or 2 amino acids from those shown in SEQ ID NOs. 53 and 61.

Particularly preferred is a human antibody (U4-3) comprising a heavy chain comprising a CDRH1 as shown in SEQ ID NO: 3, a CDRH2 as shown in SEQ ID NO: 8 and a CDRH3 as shown in SEQ ID NO: 15 and a light chain comprising a CDRL1 as shown in SEQ ID NO. 23, a CDRL2 as shown in SEQ ID NO: 25 and a CDRL3 as shown in SEQ ID NO: 30. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 54 and a light chain variable region according to SEQ ID NO: 62. Also suitable are human antibodies wherein the sequences of the variable region of the heavy chain and/or the light chain differ in 1 or 2 amino acids from those shown in SEQ ID NOs. 54 and 62.

Particularly preferred is a human antibody (U4-4) comprising a heavy chain comprising a CDRH1 as shown in SEQ ID NO: 4, a CDRH2 as shown in SEQ ID NO: 9 and a CDRH3 as shown in SEQ ID NO: 16 and a light chain comprising a COMA as shown in SEQ ID NO: 22, a CDRL2 as shown in SEQ ID NO: 24 and a CDRL3 as shown in SEQ ID NO: 31. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 55 and a light chain variable region according to SEQ ID NO: 63. Also suitable are human antibodies wherein the sequences of the variable region of the heavy chain and/or the light chain differ in 1 or 2 amino acids from those shown in SEQ ID NOs. 55 and 63.

Particularly preferred is a human antibody (U4-5) comprising a heavy chain comprising a CDRL1 as shown in SEQ ID NO: 5, a CDRH2 as shown in SEQ ID NO: 10 and a CDRL3 as shown in SEQ ID NO: 17 and a light chain comprising a CDRL1 as shown in SEQ ID NO: 22, a CDRL2 as shown in SEQ ID NO: 24 and a CDRL3 as shown in SEQ ID NO: 32. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 56 and a light chain variable region according to SEQ ID NO: 64. Also suitable are human antibodies wherein the sequences of the variable region of the heavy chain and/or the light chain differ in 1 or 2 amino acids from those shown in SEQ ID NOs, 56 and 64.

Particularly preferred is a human antibody (U4-6) comprising a heavy chain comprising a CDRH1 as shown in SEQ ID NO:6; a CDRH2 as shown in SEQ ID NO: 12 and a CDRH3 as shown in SEQ ID NO: 19 and a light chain comprising a CDRL1 as shown in SEQ ID NO: 22, a CDRL2 as shown in SEQ. ID NO: 26 and a CDRL3 as shown in SEQ ID NO: 34. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 58 and a light chain variable region according to SEQ ID NO: 66. Also suitable are human antibodies wherein the sequences of the variable region of the heavy chain and/or the light chain differ in 1 or 2 amino acids from those shown in SEQ ID NOs. 58 and 66.

Particularly preferred is a human antibody (U4-7) comprising a heavy chain comprising a CDRH1 as shown in SEQ ID NO: 3, a CDRH2 as shown in SEQ. ID NO: 7 and a CDRH3 as shown in SEQ ID NO: 20 and a light chain comprising a COMA as shown in SEQ ID NO: 68, a CDRL2 as shown in SEQ ID NO: 27 and a CDRL3 as shown in SEQ ID NO: 35. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 59 and a light chain variable region according to SEQ ID NO: 67. Also suitable are human antibodies wherein the sequences of the variable region of the heavy chain and/or the light chain differ in 1 or 2 amino acids from those shown in SEQ ID NOs. 59 and 67.

Particularly preferred is a human antibody (U4-8) comprising a heavy chain comprising a CDRH1 as shown in SEQ ID NO: 4, a CDRH2 as shown in SEQ ID NO: 11 and a CDRH3 as shown in SEQ ID NO: 18 and a light chain comprising a CDRL1 as shown in SEQ ID NO: 22, a CDRL2 as shown in SEQ ID NO: 24 and a CDRL3 as shown in SEQ ID NO: 33. Also suitable are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 57 and a light chain variable region according to SEQ ID NO: 65. Also suitable are human antibodies wherein the sequences of the variable region of the heavy chain and/or the light chain differ in 1 or 2 amino acids from those shown in SEQ ID NOs. 57 and 65.

Also preferred is a human antibody (U4-9) comprising a heavy chain comprising a CDR1 as shown in SEQ ID NO: 3, a CDRH2 as shown in SEQ ID NO: 8 and a CDRH3 as shown in SEQ ID NO: 15 and a light chain comprising a CDRL1 as shown in SEQ. ID NO: 68, a CDRL2 as shown in SEQ ID NO: 27 and a CDRL3 as shown in SEQ ID NO: 35. Also suitable are human antibodies, wherein one or more of the CDRs differ in one or two amino acids or antibodies recognizing the same epitope on human FGFR4. In a particularly preferred embodiment e human antibody comprises a heavy chain variable region according to SEQ ID NO: 54 and a light chain variable region according to SEQ ID NO: 67. The antibody U4-9 preferably comprises the heavy chain as specified for antibody U4-3 and the light chain as specified for antibody U4-7.

Furthermore, soluble FGFR4 receptors, e.g. receptor fragments without the membrane anchor domain, antagonistic FGFR4 ligand muteins, such as muteins of FGF1, FGF2, FGF4, FGF8, FGF8, FGF9, FGF1 FGF17, FGF18 or FGF19, peptides or low-molecular weight FGFR4 inhibitors may be used in the present invention, Examples of low-molecular weight inhibitors of FGFR4 are indolinones (Mohammadi et al. (1997), Science 276:955-960), SU5402, SU4984, and PD17304 (Koziczak et al. (2004), Biol. Chem.279, 50004-50011).

The invention also encompasses the administration of at least two FGFR4 inhibitors as defined above, in particular two, three, four, or five FGFR4 inhibitors.

A further aspect of the present invention refers to a pharmaceutical composition or kit comprising an FGFR4 inhibitor and an agent capable of reducing bile acid levels as specified above. Additionally, the pharmaceutical composition or kit may optionally comprise one or more physiologically acceptable carriers, diluents and/or adjuvants.

Pharmaceutical compositions or kits suitable for use in the present invention include compositions or kits wherein the active ingredients are contained in an effective amount to achieve its intended purpose. A therapeutically effective dose refers to that amount of the compounds that results in amelioration of symptoms or a prolongation of survival in a patient suffering from a hyperproliferative disorders as defined above.

Toxicity and therapeutic efficacy of the FGFR4 inhibitor and the agent capable of reducing bile acid levels can be determined by standard pharmaceutical procedures in cell cultures or experimental animals, e.g. for determining the LD50 (the dose lethal to 50% of the population) and the EDSO (the dose therapeutically effective in 50% of the population). For any compound used in the present invention, the therapeutically effective dose can be estimated initially from cell culture assays. For example, a dose can be formulated in animal models to achieve a circulating concentration range that includes the IC50 as determined in cell culture (i.e. the concentration of the test compound which achieves a half-maximal inhibition of the growth-factor receptor activity). Such information can be used to more accurately determine useful doses in humans. The dose ratio between toxic and therapeutic effects is the therapeutic index and it can be expressed as the ratio between LD50 and ED50.

Compounds which exhibit high therapeutic indices are preferred. The exact formulation, route of administration and dosage can be chosen by the individual physician in view of the patient's condition (see e.g. Fingl et al., 1975, in "The Pharmacological Basis of Therapeutics", Ch. 1, p. 1). Dosage amount and interval may be adjusted individually to provide plasma levels of the active moiety which are sufficient to maintain the receptor modulating effects, or minimal effective concentration (MEC). The MEC will vary for each compound but can be estimated from in vitro data, e.g. the concentration necessary to achieve a 50-90% inhibition of the receptor using the assays described herein. Compounds should be administered using a regimen which maintains plasma levels above the MEC for 10-90% of the time, preferably between 30-90% and most preferably between 50-90%. Dosages necessary to achieve the MEC will depend on individual characteristics and route administration. In cases of local administration or selective uptake, the effective local concentration of the drug may not be related to plasma concentration.

The pharmaceutical composition or kit of the present invention is suitable for use in the treatment of diseases as specified herein. In particular, the pharmaceutical composition or kit is suitable for use in the prevention, alleviation and/or treatment of diseases associated with FGFR4 expression, overexpression or hyperactivity. Diseases that can be treated using a pharmaceutical composition or kit of the present invention include hyperproliferative disorders, cardiovascular diseases, in particular hypertension, left ventricular hypertrophy, heart hypertrophy, chronic kidney diseases, muscular dystrophy and metabolic diseases, in particular obesity and diabetes.

Most preferably, the pharmaceutical composition or kit of the present invention is suitable for use in the treatment of hyperproliferative disorders as defined herein above.

The actual amount of the pharmaceutical composition or kit administered is dependent on the subject being treated, on the subject's weight, the severity of the affliction, the administration route and the judgement of the prescribing physician. For antibodies or therapeutical active nucleic acid molecules, and other compounds e.g. a daily dosage of 0,001 to 100 mg/kg, particularly 0.01 to 10 mg/kg per day is suitable.

Suitable routes of administration include, for example, oral, rectal, transmucosal or intestinal administration; parenteral delivery, including intramuscular, subcutaneous, intramedullary injections, as well as intrathecal, direct intraventricular, intravenous, intraperitoneal, intranasal or intraocular injections.

For the agent capable of reducing bile acid levels, in particular the bile acid sequestrant (e.g. colestyramine), oral administration is preferred. For FGFR4 inhibitors, in particular the anti-FGFR4 antibody (e.g. U4-3), intravenous administration is preferred.

Alternatively, one may administer the pharmaceutical composition or kit of the present invention in a local rather than a systematic manner, for example, via injection of the compound directly into a solid tumor, often in a depot or sustained release formulation.

Furthermore, one may administer the pharmaceutical composition or kit of the present invention in a targeted drug delivery system, for example in a liposome coated with a tumour-specific antibody. The liposomes will be targeted to and taken up selectively by the tumour.

In the pharmaceutical composition or kit of the present invention, the FGFR4 inhibitor and the agent capable of reducing bile acid levels (in particular one or more bile acid sequestrants) may be provided in one pharmaceutical composition (single dose form) or may be provided in different compositions (separate dose form), preferably at least two distinct compositions, more preferably two distinct compositions. In particular, the distinct compositions of the pharmaceutical composition or kit of the present invention may be administered by the same route or by different routes.

Yet another aspect of the present invention is a method for preventing, alleviating or/and treating diseases comprising administrating an effective amount of an FGFR4 inhibitor in co-administration with an agent capable of reducing bile acid levels (in particular one or more bile acid sequestrants) to a subject in need thereof. In particular, the diseases may be hyperproliferative disorders, cardiovascular diseases, in particular hypertension, left ventricular hypertrophy and heart hypertrophy, chronic kidney diseases, muscular dystrophy and metabolic diseases, in particular obesity and diabetes. A preferred aspect of the invention is a method for preventing alleviating or/and treating a hyperproliferative disorder as described herein above.

The subject in need of prevention, alleviation or/and treatment may be any animal which may suffer from a hyperproliferative disorder, cardiovascular disease, in particular hypertension or chronic kidney disease, in particular a mammal, more particularly a human being.

According to another aspect of the invention the combination of an FGFR4 inhibitor and an agent capable of reducing bile acid levels can be combined with a further therapeutic procedure.

The therapeutic procedure to be combined with the FGFR4 inhibitor and the agent capable of reducing bile acid levels includes any suitable therapeutic procedure suitable for the prevention, alleviation or/and treatment of a hyperproliferative disorder, in particular suitable for the induction of apoptosis in hyperproliferative cells/cancer cells. Thus the therapeutic procedure may include a treatment with an agent for the prevention, alleviation or/and treatment of a hyperproliferative disorder (with an anti-cancer drug, in particular with an apoptosis inducing agent) or/and irradiation. In a preferred embodiment, the therapeutic procedure for the prevention, alleviation or/and treatment of a hyperproliferative disorder is irradiation therapy, more preferably a gamma irradiation therapy. Radiation treatment regimens are known by a person skilled in the art. The dosage of state of the art cancer treatments may be reduced when combined with administration of an FGFR4 inhibitor and an agent capable of reducing bile acid levels.

According to the present invention, it is preferred to supplement the above-described treatment with a combination of an FGFR4 inhibitor (in particular an anti-FGFR4 antibody) and an agent capable of reducing bile acid levels (in particular a bile acid sequestrant), with administration of vitamins, in particular fat-soluble vitamins. It was found that bile acid sequestrants bind fat-soluble vitamins, such as vitamin A, vitamin D, vitamin E and vitamin K. As this effect could result in vitamin deficiency, supplementation with these vitamins is found to be beneficial. Appropriate intervals between dosing of the vitamins and bile acid sequestrants should be attended to.

The invention shall be further illustrated by the following figures and examples.

FIGURES

FIG. 1: Serum levels of bilirubin, γ-glutamyltransferase and alkaline phosphatase. The results are shown for administration of U4-3 alone (●), U4-3 in combination with Ursofalk™ (■) and U4-3 in combination with Quantalan™ (▲). Dotted vertical lines: U4-3 administration, palliative therapy started with U4-3 on day 0, first measurement after administration was on day 1.

Figure 2A:
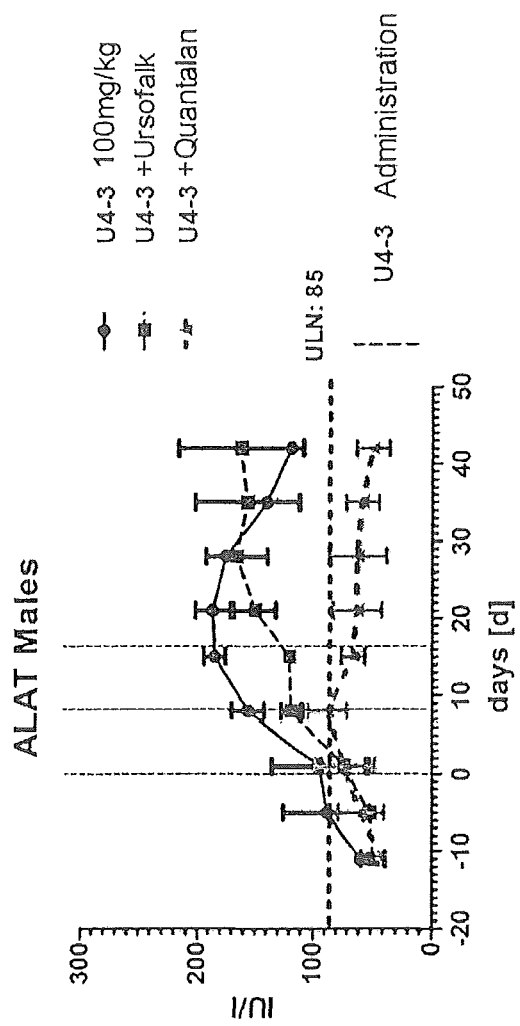
Figure 2B:
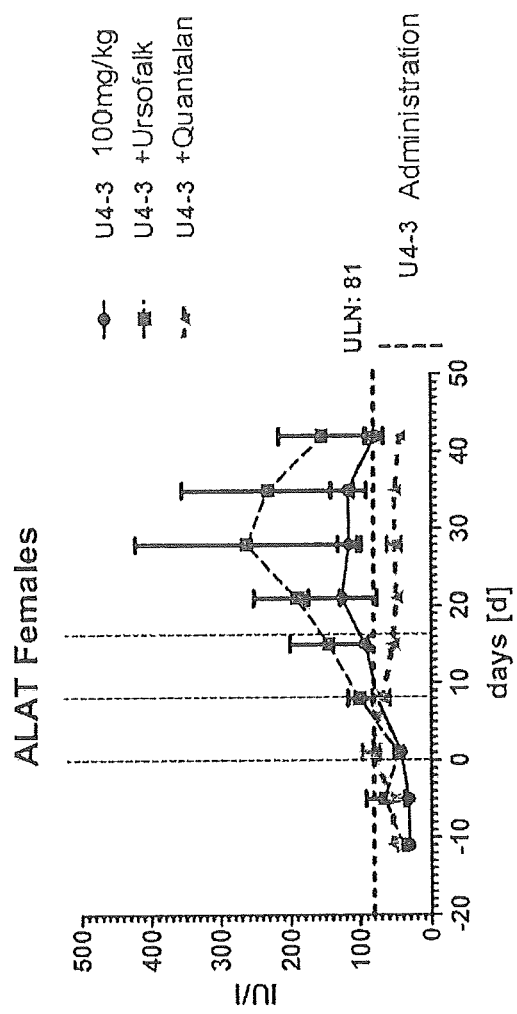

FIGS. 2a-2b: Alaninaminotransferase (ALA T) in serum of cynomolgus monkeys. Upper limit of normal (ULN): 81 UI/I. The results are shown for male monkeys in FIG. 2a and for female monkeys in FIG. 2b. The values shown as ● represent administration of U4-3 alone, ■ represents U4-3 in combination with Ursofalk™ and ▲ represents U4-3 in combination with Quantalan™. Dotted lines show the time of U4-3 administration.

Figure 3:
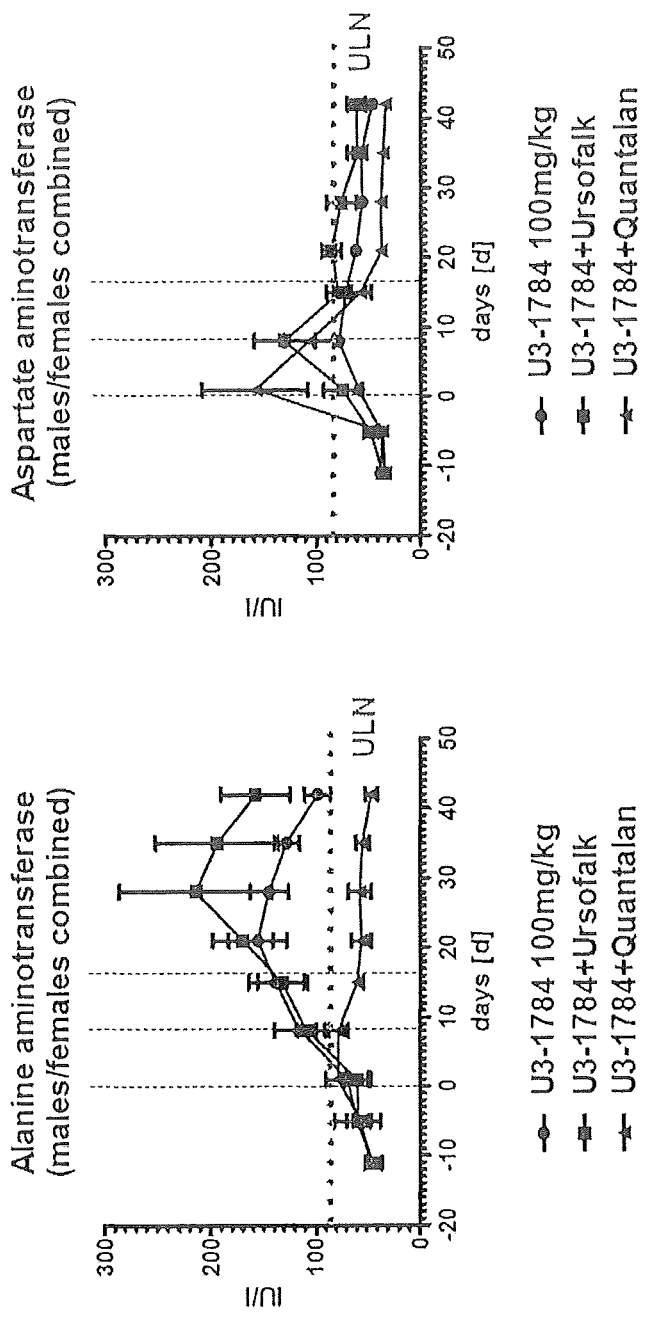

FIG. 3: Levels of alanine aminotransferase (ALT) and aspartate aminotransferase (AST) as an indicator of liver function. The results are shown for administration of U4-3 alone (●), U4-3 in combination with Ursofalk™ (■) and U4-3 in combination with Quantalan™ (▲). Dotted vertical lines illustrate the time of U4-3 administration.

Figure 4A:
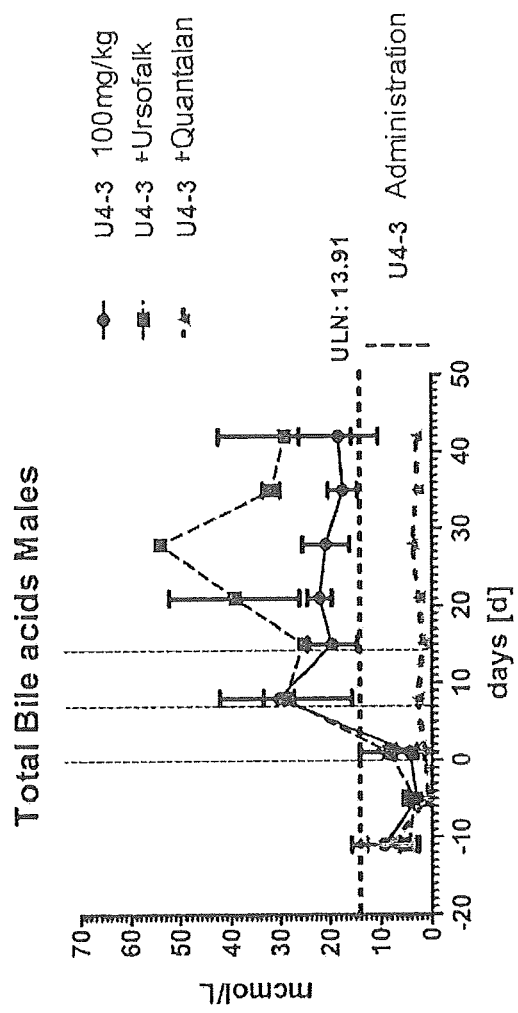
Figure 4B:
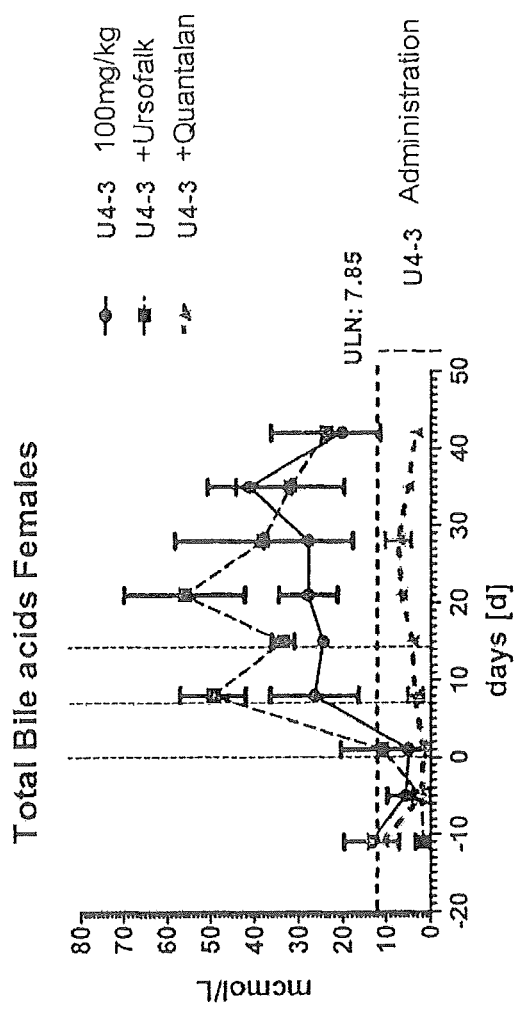

FIGS. 4a-4b: Total bile acid levels in serum of cynomolgus monkeys. ULN: 13.91 in males, 7.85 in females. The results are shown for male animals in FIG. 4a and for females in FIG. 4b. ● represents values obtained for U4-3 alone, represents U4-3 in combination with Ursofalk™ and ▲ represents U4-3 in combination with Quantalan™. Dotted lines illustrate the time of U4-3 administration.

Figure 5A:
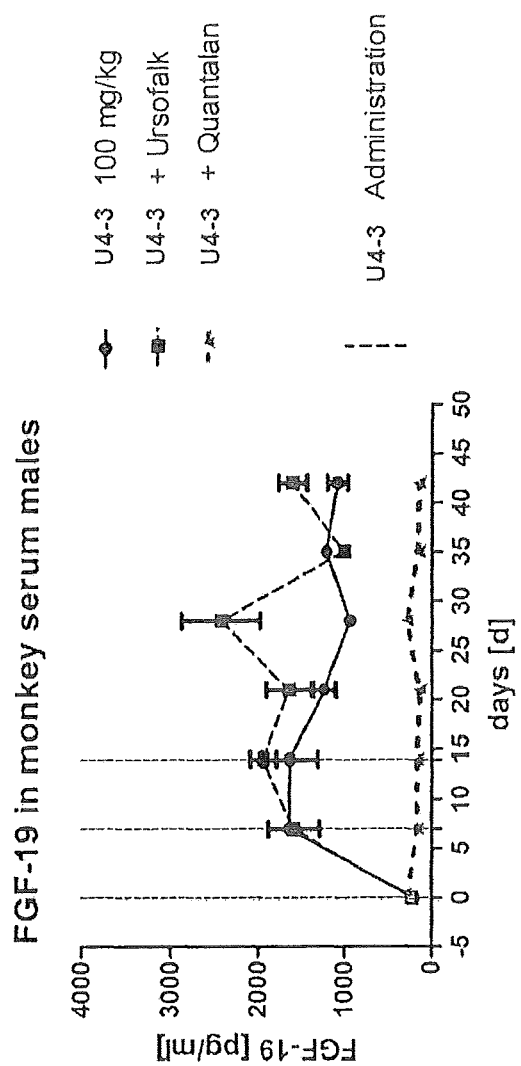
Figure 5B:
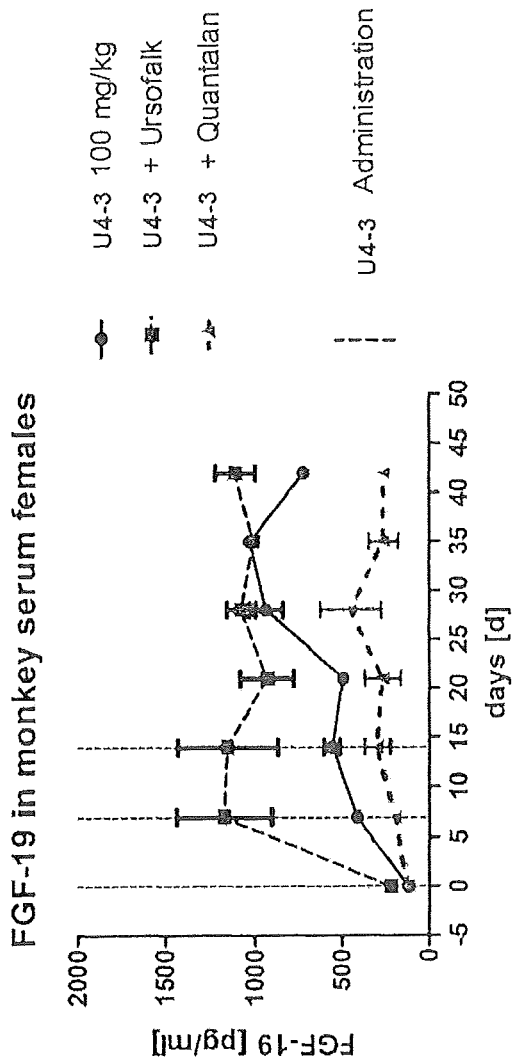
Figure 5C:
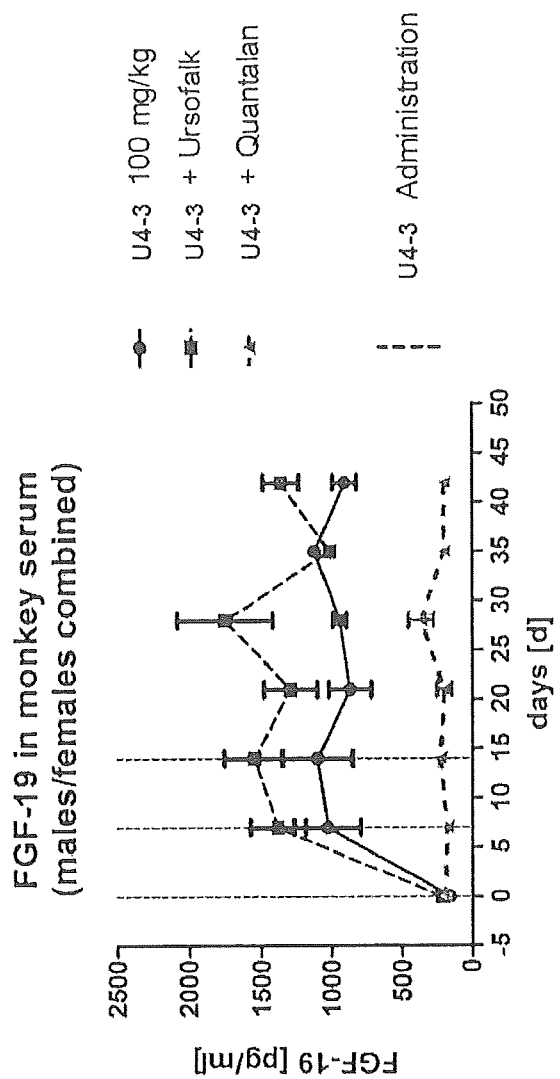

FIGS. 5a-5b: FGF19 in serum of cynomolgus monkeys. The results are shown for male animals in FIG. 5a, for females in FIG. 3b and the combined results are shown in FIG. 5c. Values shown with represents administration of U4-3 alone, ■ represents U4-3 in combination with Ursofalk™ and ● represents U4-3 in combination with Quantalan™. Dotted lines illustrate the time of U4-3 administration.

Figure 6:
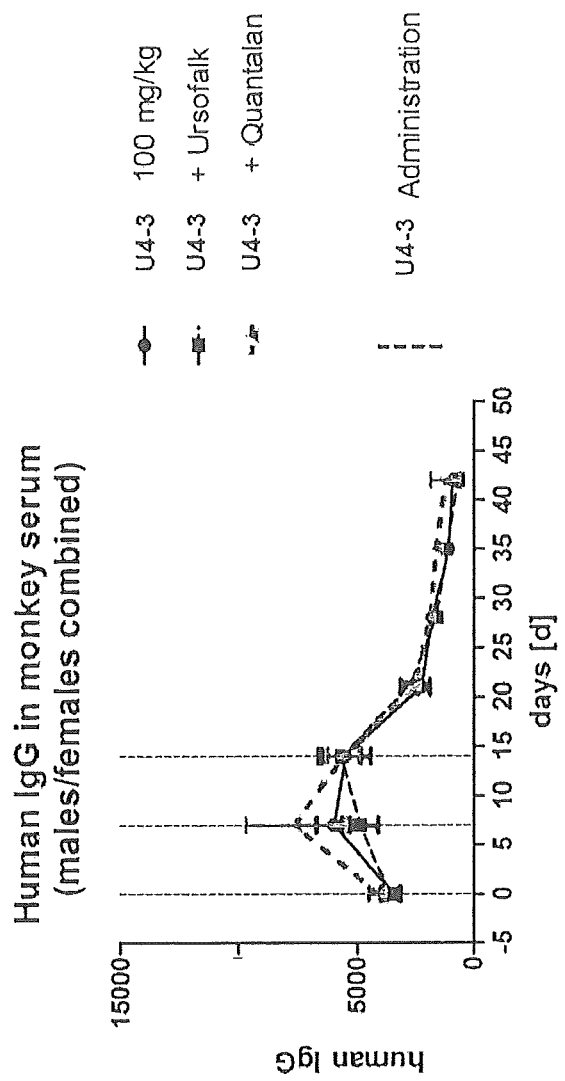

FIG. 6: Human IgG in monkey serum. The results shown were obtained for the combination of male and female animals. Values shown with ● represent administration of U4-3 alone, ■ represents U4-3 in combination with Ursofalk™ and ▲ represents U4-3 in combination with Quantalan™. Dotted lines illustrate the time of U4-3 administration.

Figure 7:
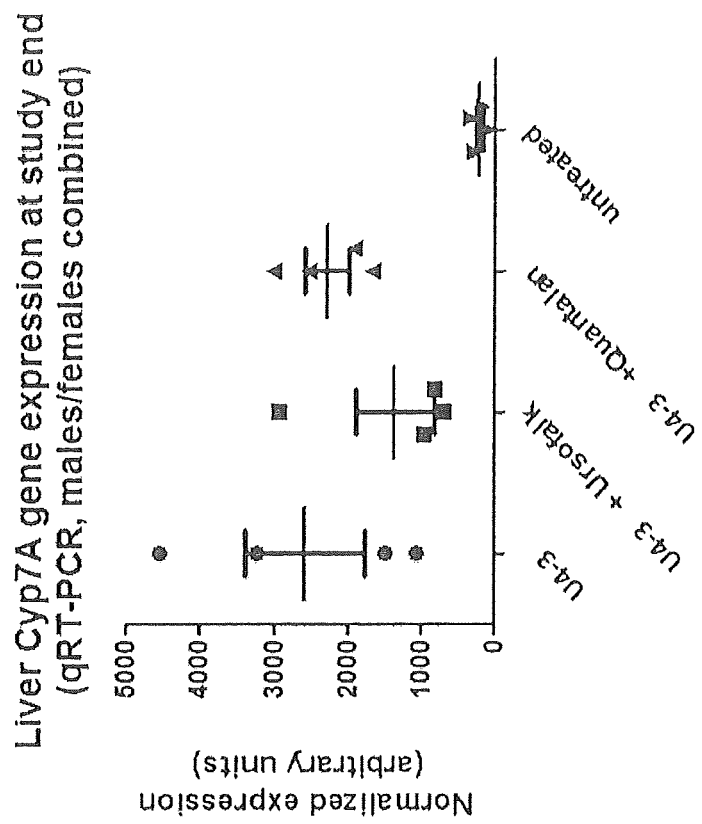

FIG. 7: Gene expression of liver Cyp7A at the end of the study. The results are shown for the administration of U4-3 alone (●), U4-3 in combination with Ursofalk™ (■), and U4-3 in combination with Quantalan™ (▲), in comparison to the untreated control group (▼).

Figure 8:
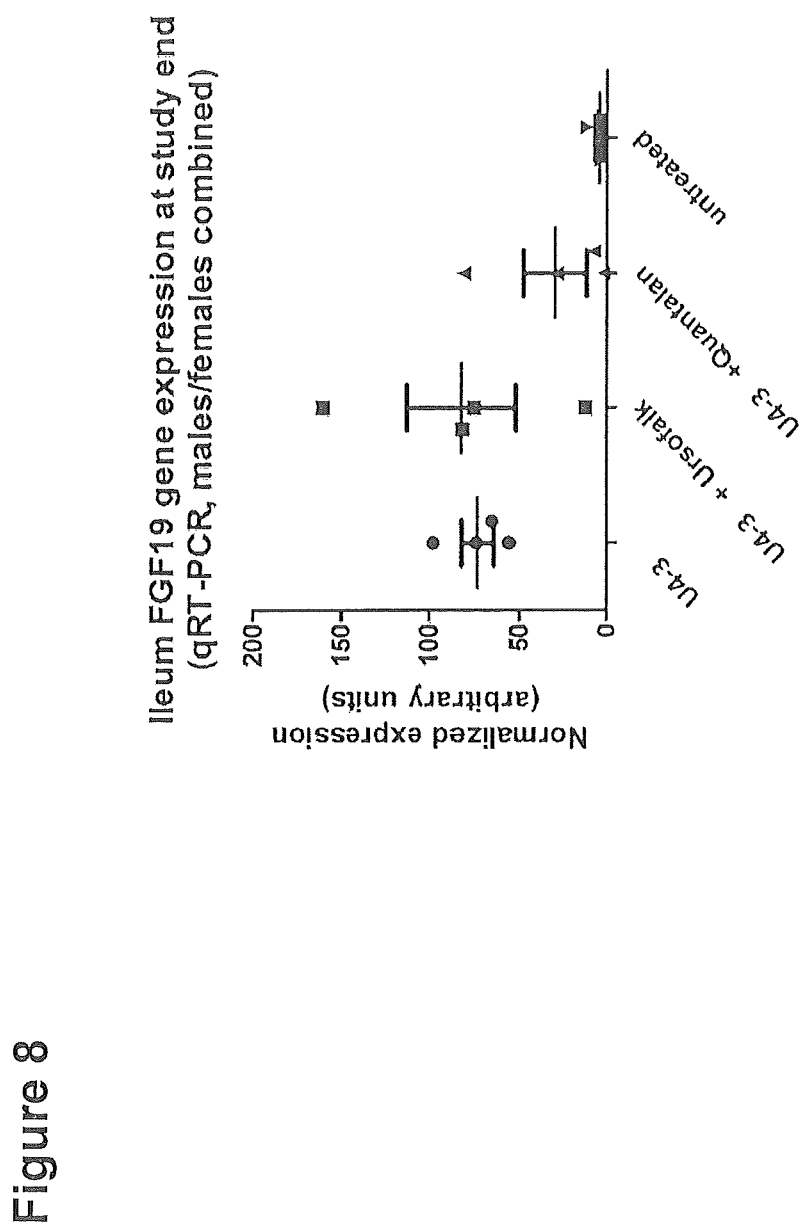

FIG. 8: Ileum FGF19 gene expression at the end of the study. The results are shown for the administration of U4-3 alone (●), U4-3 in combination with Ursofalk™ (■), and U4-3 in combination with Quantalan™ (▲), in comparison to the untreated control group (▼).

EXAMPLES

Toxicity of FGFR4 Inhibitors in the Presence and Absence of an Agent Capable of Reducing Bile Acid Levels In order to find ort whether any toxic side effects of FGFR4 inhibition are due to elevated bile acid levels, the effect of co-administering agents which interfere with bile acid levels was examined. The anti-FGFR4 antibody U4-3 was used as inhibitor of FGFR4 activity (Test Item: TI). For reducing bile acid levels, the bile acid sequestrant colestyramine (Quantalan™) was used. Ursodeoxycholic acid (Ursofalk™) was used as a second compound for increasing the transport of bile acids out of the liver. Ursodeoxycholic acid is a hydrophilic bile acid that increases bile acid transporter expression and plasma membrane translocation in the liver, (palliative compounds 1 and 2).

The study design included four cynomolgus monkeys (two male, two female) per group. The animals were assigned to the following groups

| | | Test item | | | Palliative compound | | |
|---|---|---|---|---|---|---|---|
| Group | Treatment | Dose level (mg/kg) | Dose volume (mL/kg) | Dose concentration (mg/mL) | Dose level [a] (mg/kg/adm) | Dose volume (ml/kg/adm) | Dose concentration (mg/mL) |
| 1 | TI | 100 | 9.52 | 10.5 | 0 | 2.5 | 0 |
| 2 | TI + PC1 | 100 | 9.52 | 10.5 | 10 | 2.5 | 4 |
| 3 | TI + PC2 | 100 | 9.52 | 10.5 | 175 | 2.5 | 70 |

[a] the daily dose level is given in twice at 8 hours ± 1 hour apart, i.e. a dose level of 20 mg/kg/day for palliative compound 1 and 350 mg/kg/day for palliative compound 2.
adm: administration;
TI: test item (U4-3);
PC1: palliative compound 1 (Quantalan1 ™);
PC2: palliative compound 2 (Ursofalk ™)

Administration
Test item (U4-3)
Route: intravenous, slow bolus infusion.
Duration and frequency: three administrations at 7-day interval (i.e. day 0, day 7 and day 14). The first day of dosing was designated as day 0. After the last administration, the animals were kept for a treatment-free period of at east 28 days.
Method: intravenous injection (slow bolus) using a pump system and a microflex infusion set introduced into a vein after local disinfection with an aqueous solution of ethyl alcohol. After injection, the vein was flushed with sterile physiological saline.
Three veins were used in rotation:
Right external saphenous vein: site 1.
Left external saphenous vein: site 2.
Right cephalic vein: site 3.
Volume administered: 9.52 mL/kg/day. Individual dose volumes were calculated using the latest body weight.
Duration of dosing: approximately 15 minutes.
Rationale for choice of route of administration: the intravenous route selected as this is a potential route of administration in humans.
Palliative Compounds and Vehicle
Route: oral.
Frequency: twice daily at 8 hours±1 hour apart.
Duration: each day from day 0 to the last day of treatment-free period, i.e. at least 41 days of administrations.
Method: naso-gastric intubation (animals are trained to this administration rotate five days before the start of treatment).
Fruit or vegetable was given before the daily administration; pelleted diet was given after the daily administration. Palliative compounds were maintained under magnetic stirring from 15 minutes before and during the dosing.
Volume administered: 2.5 mL/adm. Individual dose volumes were calculated using the latest body weight.
Rationale for choice of route of administration: the oral route was selected as this is the route of administration in humans.
Observations
The test animals were examined for clinical signs, liver enzymes, bile acid levels and FGF19. FGF19 serum levels were determined using quantiquine human FGF19 ELISA from RND according to the manufacturer's instructions. RNA expression of cyno liver and ileum samples for Cyp7A1 (liver) and FGF19 (Ileum) were determined using the High-Capacity RNA-to-cDNA Kit (Applied Biosystems/Life Technologies) followed by subsequent quantitative real-time PCR. The results are shown in FIGS. 1-8 and in Table 1 below.

Liver enzyme levels in the serum of cynomolgous monkeys were determined to show that enzyme levels by bilirubin, γ-glutamyltransferase and alkaline phosphatase are not affected by administering the FGFR4 inhibitor with or without bile acid-modifyingagents. (FIG. 1) Elevated levels of liver enzymes (ALAT), bile acids and FGF19 were found in cynomolgus serum after U4-3 administration in line with the suggested biological function of FGFR4 in bile acid level regulation. Some animals also showed minimal bile duct hyperplasia after histopathological examination of the liver. All these increases and changes were abolished by co-administration of Quantalan™ (colestyramine). With Ursofalk™, the effect was less pronounced (FIGS. 2 to 5). Human IgG levels in serum were equal in all treatment groups showing that Quantalan™ and
Ursofalk™ did not work by simply reducing serum antibody levels (FIG. 6) as can be expected by the different organ compartments in which the co-treatments work (FGFR4 in blood accessible organs like the liver whereas Quantalan™ and Ursofalk™ are oral compounds and Quantalan™ is directly excreted without crossing into the blood stream). The elevated liver Cyp7A gene expression at study end shows that the FCFR4 antibody inhibits liver FGFR4 in all treatment groups until the end of the study further supporting that the FGFR4 inhibitor function of the antibody is unchanged by the co-administered compounds (FIG. 7). Co-adminstration of Quantalan™ (colestyramine) with the FGFR4 antibody also prevented the elevated FGF19 expression levels in the ileum compared to FGFR4 antibody alone. This reiterates that bile acids upregulate FGF19 in the gut (FIG. 8).

TABLE 1

Overview of the changed blood clinical chemistry values in the cyno study (100 mg/kg weekly × 3 + 28 d recovery)

| | Male (100 mg/kg/adm) | | |
|---|---|---|---|
| | pretest | day 14 | day 42 |
| Bile acids (μmol/L) | 2.31 | 42.90 | 24.16 |
| Alkaline phosphatase (IU/L) | 1985 | 2452 | 2490 |
| Aspartate aminotransferase (IU/L) | 43 | 158 | 119 |
| Alanine aminotransferase (IU/L) | 37 | 234 | 223 |

| | Female (100 mg/kg/adm) | | |
|---|---|---|---|
| | pretest | day 14 | day 42 |
| Bile acids (μmol/L) | 1.08 | 69.14 | 21.77 |
| Alkaline phosphatase (IU/L) | 1030 | 1410 | 1200 |
| Aspartate aminotransferase (IU/L) | 34 | 192 | 57 |
| Alanine aminotransferase (IU/L) | 35 | 332 | 131 |

Conclusion

Under the defined experimental conditions, three intravenous administrations of U4-3, 7 days apart at the dose level of 100 mg/kg, alone or associated with two different palliative compounds (Ursofalk™ at 20 mg/kg/day or Quantalan™ at 350 mg/kg/day; oral administration twice a day at 8 hours apart) were clinically well tolerated, without clinical signs, local reaction, nor effect on food consumption or body weight. Elevated serum bile acids and liver enzyme levels (aspartate aminotransferase and alanine aminotransferase) were noted in animals receiving the FGFR4 inhibitor alone or together with the palliative compound 1, Ursofalk™.

Treatment with the test item associated with palliative compound 2, Quantalan™, only induced transient aspartate aminotransferase activity. The effect was reversible at the end of the 4-week treatment-free period. The addition of Quantalan™ permitted to maintain bile acid concentration (FIG. 2) and alanine aminotransferase activity within the normal range (FIG. 3) and there were no histopathological changes The histopathological examination did not reveal any item-related findings.

Administration of Ursofalk™ or Quantalan™ as adjunct treatment had no impact on the systemic exposure to U4-3.

Based on these findings, the test item U4-3 at the dose level of 100 mg/kg was considered to be better tolerated when it was administered in association with the palliative compound 2, Quantalan™.

The study therefore confirmed that side effects of the administration of an FGFR4 inhibitor (U4-3) can be significantly reduced by additionally administering an agent capable of reducing bile acid levels (in particular colestyramine). The combination therapy of U4-3 and colestyramine resulted in no toxicological findings (clinical signs, hematology, blood chemistry and histopathology), whereas these parameters have been found elevated after treatment with U4-3 alone.

The present specification also includes an ASCII text file entitled "WK10053-0004USD1-59300PEP-ST25-replacement-seq-listing-FINAL-10-13-20.txt" that was created on Oct. 13, 2020, and has a file size of 42,527 bytes, the subject matter of which is incorporated by reference in its entirety.

---

The invention claimed is:

1. A method for treating hepatocellular carcinoma, said method comprising administrating an effective amount of an FGFR4 inhibitor combination comprising an anti-FGFR4 antibody in combination with colestyramine to a subject in need thereof, wherein the anti-FGFR4 antibody comprises a heavy chain comprising a CDRH1 as shown in SEQ ID NO: 3, a CDRH2 as shown in SEQ ID NO: 8 and a CDRH3 as shown in SEQ ID NO: 15 and a light chain comprising a CDRL 1 as shown in SEQ ID NO: 23, a CDRL2 as shown in SEQ ID NO: 25 and a CDRL3 as shown in SEQ ID NO: 30.

2. The method of claim 1, further comprising administering one or more fat-soluble vitamins to the subject.

3. The method of claim 1, wherein the anti-FGFR4 antibody and the colestyramine are administered together or separately, wherein the anti-FGFR4 antibody is intravenously administered and the colestyramine is orally administered.

4. The method of claim 1, wherein the anti-FGFR4 antibody and the colestyramine are administered in a single dose or divided in two or three doses per day.

5. The method of claim 1, wherein the anti-FGFR4 antibody and the colestyramine are administered separately and wherein the anti-FGFR4 antibody is administered in a single dose and the colestyramine is administered in two or three doses per day.

* * * * *

SEQUENCE LISTING

```
<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: U4-1-VH CDRH1

<400> SEQUENCE: 1

Arg Asn Tyr Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: U4-2-VH CDRH1

<400> SEQUENCE: 2

Lys Ala Trp Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: U4-3-VH, U4-7-VH and U4-9-VH CDRH1

<400> SEQUENCE: 3

Asp Tyr Tyr Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: U4-4-VH and U4-8-VH CDRH1

<400> SEQUENCE: 4

Ser Asn Tyr Met Ser
```

```
1               5

<210> SEQ ID NO 5
<211> LENGTH: 5
<212> TYPE: PRT
<213> ORGANISM: Artificial Sequence
<220> FEATURE:
<223> OTHER INFORMATION: U4-5-VH CDRH1

<400> SEQUENCE: 5

Ser Asn Tyr Met Asn
1               5

<210> SEQ ID NO 6
<211> LENGTH: 5
<212> TYPE: PRT
<213> ORGANISM: Artificial Sequence
<220> FEATURE:
<223> OTHER INFORMATION: U4-6-VH CDRH1

<400> SEQUENCE: 6

Asp Tyr Tyr Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: U4-1-VH, U4-2-VH and U4-7-VH CDRH2

<400> SEQUENCE: 7

Ala Ile Ser Gly Ser Gly Gly Ser Thr Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: U4-3-VH and U4-9-VH CDRH2

<400> SEQUENCE: 8

Thr Ile Ser Gly Ser Gly Gly Ser Thr Tyr Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: U4-4-VH CDRH2

<400> SEQUENCE: 9

Leu Ile Ser Gly Ser Gly Gly Ser Thr Tyr Tyr Ala Asp Ser Val Gln
1               5                   10                  15

Gly

<210> SEQ ID NO 10
<211> LENGTH: 17
<212> TYPE: PRT
<213> ORGANISM: Artificial Sequence
<220> FEATURE:
```

```
<223> OTHER INFORMATION: U4-5-VH CDRH2

<400> SEQUENCE: 10

Val Ile Ser Tyr Asp Gly Ser Asn Lys Tyr Tyr Ala Asp Ser Val Lys
1               5                   10                  15
Gly

<210> SEQ ID NO 11
<211> LENGTH: 17
<212> TYPE: PRT
<213> ORGANISM: Artificial Sequence
<220> FEATURE:
<223> OTHER INFORMATION: U4-8-VH CDRH2

<400> SEQUENCE: 11

Ser Ile Ser Gly Ser Gly Gly Arg Thr Tyr Tyr Ala Asp Ser Val Lys
1               5                   10                  15
Gly

<210> SEQ ID NO 12
<211> LENGTH: 17
<212> TYPE: PRT
<213> ORGANISM: Artificial Sequence
<220> FEATURE:
<223> OTHER INFORMATION: U4-6-VH CDRH2

<400> SEQUENCE: 12

Ala Ile Gly Gly Ser Gly Asp Arg Thr Tyr Tyr Ala Asp Ser Val Lys
1               5                   10                  15
Gly

<210> SEQ ID NO 13
<211> LENGTH: 9
<212> TYPE: PRT
<213> ORGANISM: Artificial Sequence
<220> FEATURE:
<223> OTHER INFORMATION: U4-1-VH CDRH3

<400> SEQUENCE: 13

Val Thr Ser Pro Gly Ala Phe Asp Ile
1               5

<210> SEQ ID NO 14
<211> LENGTH: 9
<212> TYPE: PRT
<213> ORGANISM: Artificial Sequence
<220> FEATURE:
<223> OTHER INFORMATION: U4-2-VH CDRH3

<400> SEQUENCE: 14

Leu Tyr Ser Tyr Gly Asp Phe Asp His
1               5

<210> SEQ ID NO 15
<211> LENGTH: 9
<212> TYPE: PRT
<213> ORGANISM: Artificial Sequence
<220> FEATURE:
<223> OTHER INFORMATION: U4-3-VH and U4-9-VH CDRH3

<400> SEQUENCE: 15

Leu Thr Ala Tyr Gly His Val Asp Ser
1               5
```

-continued

```
<210> SEQ ID NO 16
<211> LENGTH: 10
<212> TYPE: PRT
<213> ORGANISM: Artificial Sequence
<220> FEATURE:
<223> OTHER INFORMATION: U4-4-VH CDRH3

<400> SEQUENCE: 16

Asn Thr Ala Gly Phe Gly Tyr Phe Asp Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: U4-5-VH CDRH3

<400> SEQUENCE: 17

Lys Ser Arg Asp Phe Trp Arg Gly Pro Phe Asp Tyr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: U4-8-VH CDRH3

<400> SEQUENCE: 18

Met Thr Val Phe Gly Ala Ala Thr Leu
1               5

<210> SEQ ID NO 19
<211> LENGTH: 7
<212> TYPE: PRT
<213> ORGANISM: Artificial Sequence
<220> FEATURE:
<223> OTHER INFORMATION: U4-6-VH CDRH3

<400> SEQUENCE: 19

Gly Gly Ser Tyr Phe Gly Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: U4-7-VH CDRH3

<400> SEQUENCE: 20

Leu Ala Thr Tyr Gly Pro Phe Asp Asp
1               5

<210> SEQ ID NO 21
<211> LENGTH: 13
<212> TYPE: PRT
<213> ORGANISM: Artificial Sequence
<220> FEATURE:
<223> OTHER INFORMATION: U4-1-VL CDRL1

<400> SEQUENCE: 21

Ser Gly Gly Thr Ser Asn Ile Gly Thr Asn Thr Val Asn
1               5                   10

<210> SEQ ID NO 22
```

```
<211> LENGTH: 13
<212> TYPE: PRT
<213> ORGANISM: Artificial Sequence
<220> FEATURE:
<223> OTHER INFORMATION: U4-2-VL, U4-4-VL, U4-5-VL, U4-6-VL and U4-8-VL
      CDRL1

<400> SEQUENCE: 22

Ser Gly Ser Ser Ser Asn Ile Gly Ser Asn Thr Val Asn
1               5                   10

<210> SEQ ID NO 23
<211> LENGTH: 13
<212> TYPE: PRT
<213> ORGANISM: Artificial Sequence
<220> FEATURE:
<223> OTHER INFORMATION: U4-3-VL CDRL1

<400> SEQUENCE: 23

Ser Gly Ser Ser Ser Asn Ile Gly Thr Asn Thr Val Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: U4-1-VL, U4-2-VL, U4-4-VL, U4-5-VL and U4-8-VL
      CDRL2

<400> SEQUENCE: 24

Arg Asn Asn Gln Arg Pro Ser
1               5

<210> SEQ ID NO 25
<211> LENGTH: 7
<212> TYPE: PRT
<213> ORGANISM: Artificial Sequence
<220> FEATURE:
<223> OTHER INFORMATION: U4-3-VL CDRL2

<400> SEQUENCE: 25

Arg Asn Tyr Gln Arg Pro Ser
1               5

<210> SEQ ID NO 26
<211> LENGTH: 7
<212> TYPE: PRT
<213> ORGANISM: Artificial Sequence
<220> FEATURE:
<223> OTHER INFORMATION: U4-6-VL CDRL2

<400> SEQUENCE: 26

Tyr Asp Asp Leu Leu Pro Ser
1               5

<210> SEQ ID NO 27
<211> LENGTH: 7
<212> TYPE: PRT
<213> ORGANISM: Artificial Sequence
<220> FEATURE:
<223> OTHER INFORMATION: U4-7-VL and U4-9-VL CDRL2

<400> SEQUENCE: 27

Arg Asn Asn Arg Arg Pro Ser
1               5
```

```
<210> SEQ ID NO 28
<211> LENGTH: 13
<212> TYPE: PRT
<213> ORGANISM: Artificial Sequence
<220> FEATURE:
<223> OTHER INFORMATION: U4-1-VL CDRL3

<400> SEQUENCE: 28

Ala Ala Trp Asp Asp Ser Leu Asn Gly Pro Tyr Val Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: U4-2-VL CDRL3

<400> SEQUENCE: 29

Ala Ala Trp Asp Asp Ser Leu Asn Gly Pro Ala Val Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: U4-3-VL CDRL3

<400> SEQUENCE: 30

Ala Ala Trp Asp Asp Ser Leu Ser Gly Pro His Val Val
1               5                   10

<210> SEQ ID NO 31
<211> LENGTH: 13
<212> TYPE: PRT
<213> ORGANISM: Artificial Sequence
<220> FEATURE:
<223> OTHER INFORMATION: U4-4-VL CDRL3

<400> SEQUENCE: 31

Ala Ala Trp Asp Asp Ser Leu Asn Gly Pro Leu Val Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: U4-5-VL CDRL3

<400> SEQUENCE: 32

Ser Thr Trp Asp Asp Ser Leu Arg Gly Trp Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: U4-8-VL CDRL3

<400> SEQUENCE: 33

Ala Ala Trp Asp Asp Ser Leu Asn Gly Pro Tyr Trp Val
1               5                   10

<210> SEQ ID NO 34
```

```
<211> LENGTH: 11
<212> TYPE: PRT
<213> ORGANISM: Artificial Sequence
<220> FEATURE:
<223> OTHER INFORMATION: U4-6-VL CDRL3

<400> SEQUENCE: 34

Ala Ala Trp Asp Asp Ser Leu Asn Gly Pro Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: U4-7-VL and U4-9-VL CDRL3

<400> SEQUENCE: 35

Ala Ala Trp Asp Asp Ser Leu Ser Gly Pro Asn Val Val
1               5                   10

<210> SEQ ID NO 36
<211> LENGTH: 354
<212> TYPE: DNA
<213> ORGANISM: Artificial Sequence
<220> FEATURE:
<223> OTHER INFORMATION: U4-1-VH

<400> SEQUENCE: 36
gaggtgcagc tgttggagtc tgggggaggc ttggtacagc ctgggggtc cctgagactc      60 tcctgtgcag cctctggatt caccttcagt agaaactaca tgagttgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac actgccgtgt attactgtgc gagagttacc    300
tcaccagggg cttttgatat ctggggccaa ggtaccctgg tcaccgtgag ctca          354

<210> SEQ ID NO 37
<211> LENGTH: 399
<212> TYPE: DNA
<213> ORGANISM: Artificial Sequence
<220> FEATURE:
<223> OTHER INFORMATION: U4-2-VH

<400> SEQUENCE: 37
gaggtgcagc tgttggagtc tgggggaggc ttggtacagc ctgggggtc cctgagactc      60 tcctgtgcag cctctggatt caccttcagt aaagcctgga tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac actgccgtgt attactgtgc gagattatac    300
agctatggtg actttgacca ctggggccaa ggtaccctgg tcaccgtgag ctcagcctcc    360
accaagggcc caagcgtctt ccccctggca ccctcctcc                          399

<210> SEQ ID NO 38
<211> LENGTH: 399
<212> TYPE: DNA
<213> ORGANISM: Artificial Sequence
<220> FEATURE:
<223> OTHER INFORMATION: U4-3-VH and U4-9-VH

<400> SEQUENCE: 38
```

```
gaggtgcagc tgttggagtc tgggggaggc ttggtacagc ctgggggggtc cctgagactc     60 tcctgtgcag cctctggatt caccttcagt gactactaca tgagctggat ccgccaggct    120
ccagggaagg ggctggagtg gtctcaact attagtggta gtggtggtag tacatactac    180
gcagactccg tgaagggccg gttcaccatc tccagagaca attccaagaa cacgctgtat    240
ctgcaaatga acagcctgag agccgaggac actgccgtgt attactgtgc cagactcacc    300
gcctatggcc acgtagactc ctggggccaa ggtaccctgg tcaccgtgag ctcagcctcc    360
accaagggcc caagcgtctt ccccctggca ccctcctcc                           399
```

<210> SEQ ID NO 39
<211> LENGTH: 402
<212> TYPE: DNA
<213> ORGANISM: Artificial Sequence
<220> FEATURE:
<223> OTHER INFORMATION: U4-4-VH

<400> SEQUENCE: 39

```
gaggtgcagc tgttggagtc tgggggaggc ttggtacagc ctgggggggtc cctgagactc     60 tcctgtgcag cctctggatt caccttcagt agcaactaca tgagctgggt ccgccaggct    120
ccagggaagg ggctggagtg gtctcactt attagtggta gtggtggtag cacatactac    180
gcagactccg tgcagggccg cttcaccatc tccagagaca attccaagaa cacgctgtat    240
ctgcaaatga acagcctgag agccgaggac actgccgtgt attactgtgc gagaaatacg    300
gctggttttg ggtacttcga tctctggggc caaggtaccc tggtcaccgt gagctcagcc    360
tccaccaagg gcccaagcgt cttccccctg caccctcct cc                        402
```

<210> SEQ ID NO 40
<211> LENGTH: 408
<212> TYPE: DNA
<213> ORGANISM: Artificial Sequence
<220> FEATURE:
<223> OTHER INFORMATION: U4-5-VH

<400> SEQUENCE: 40

```
gaggtgcagc tgttggagtc tgggggaggc ttggtacagc ctgggggggtc cctgagactc     60 tcctgtgcag cctctggatt caccttcagt agcaactaca tgaactgggt ccgccaggct    120
ccagggaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac actgccgtgt attactgtgt gacaaagtct    300
cgagattttt ggcggggtcc ctttgactac tggggccaag gtaccctggt caccgtgagc    360
tcagcctcca ccaagggccc aagcgtcttc ccctggcac cctcctcc                  408
```

<210> SEQ ID NO 41
<211> LENGTH: 399
<212> TYPE: DNA
<213> ORGANISM: Artificial Sequence
<220> FEATURE:
<223> OTHER INFORMATION: U4-8-VH

<400> SEQUENCE: 41

```
gaggtgcagc tgttggagtc tgggggaggc ttggtacagc ctgggggggtc cctgagactc     60 tcctgtgcag cctctggatt caccttcagt agcaactaca tgagctgggt ccgccaggct    120
ccagggaagg ggctggagtg gtctcaagt attagtggta gtggtggtcg cacatactac    180
```

```
gcagactccg tgaagggccg attcaccatc tccagagaca attccaagaa cacgctgtat    240
ctgcaaatga acagcctgag agccgaggac actgccgtgt attactgtgc gagaatgacg    300
gtctttggag cggcaacgct cggggccaa ggtaccctgg tcaccgtgag ctcagcctcc    360
accaagggcc caagcgtctt ccccctggca cctcctcc                            399

<210> SEQ ID NO 42
<211> LENGTH: 393
<212> TYPE: DNA
<213> ORGANISM: Artificial Sequence
<220> FEATURE:
<223> OTHER INFORMATION: U4-6-VH

<400> SEQUENCE: 42
gaggtgcagc tgttggagtc tgggggaggc ttggtacagc ctgggggtc cctgagactc      60 tcctgtgcag cctctggatt caccttcagt gactactaca tgaactgggt ccgccaggct    120
ccaggcaagg gctggagtg gtctcagct attggtggta gtggtgatag aacatactac    180
gcagactccg tgaagggccg gttcaccatc tccagagaca attccaagaa cacgctgtat    240
ctgcaaatga acagcctgag agccgaggac actgccgtgt attactgtgc tctcggtggg    300
agctacttcg gctactgggg ccaaggtacc ctggtcaccg tgagctcagc ctccaccaag    360
ggcccaagcg tcttcccct ggcaccctcc tcc                                 393

<210> SEQ ID NO 43
<211> LENGTH: 399
<212> TYPE: DNA
<213> ORGANISM: Artificial Sequence
<220> FEATURE:
<223> OTHER INFORMATION: U4-7-VH

<400> SEQUENCE: 43
gaggtgcagc tgttggagtc tgggggaggc ttggtacagc ctgggggtc cctgagactc      60 tcctgtgcag cctctggatt caccttcagt gactactaca tgagctgggt ccgccaggct    120
cccgggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac actgccgtgt attactgtgc gaccctggcc    300
acctacggac catttgacga ctggggccaa ggtaccctgg tcaccgtgag ctcagcctcc    360
accaagggcc caagcgtctt ccccctggca cctcctcc                           399

<210> SEQ ID NO 44
<211> LENGTH: 345
<212> TYPE: DNA
<213> ORGANISM: Artificial Sequence
<220> FEATURE:
<223> OTHER INFORMATION: U4-1-VL

<400> SEQUENCE: 44
cagtctgtgc tgactcagcc accctcagcg tctgggaccc ccgggcagag ggtcaccatc      60
tcttgttctg gaggcaccctc caacatcgga actaatactg taaactggta tcagcagctc    120
ccaggaacgg cccccaaact cctcatctat aggaataatc agcggccctc agggtccct    180 gaccgattct ctggctccaa gtctggcacc tcatcctccc tggccatcag tgggctccgg    240
tccgaggatg aggctgatta ttactgtgca gcatgggatg acagcctgaa tggtccctat    300
gtggtattcg gcggaggaac caagctgacg gtcctaggtc agcct                    345
```

<210> SEQ ID NO 45
<211> LENGTH: 345
<212> TYPE: DNA
<213> ORGANISM: Artificial Sequence
<220> FEATURE:
<223> OTHER INFORMATION: U4-2-VL

<400> SEQUENCE: 45

```
cagtctgtgc tgactcagcc accctcagcg tctgggaccc ccgggcagag ggtcaccatc     60
tcttgttctg gaagcagctc caacatcgga agtaatactg taaactggta tcagcagctc    120
ccaggaacgg cccccaaact cctcatctat cggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtcccgct    300
gtggtattcg gcggaggaac caagctgacg gtcctaggtc agcct                    345
```

<210> SEQ ID NO 46
<211> LENGTH: 345
<212> TYPE: DNA
<213> ORGANISM: Artificial Sequence
<220> FEATURE:
<223> OTHER INFORMATION: U4-3-VL

<400> SEQUENCE: 46

```
cagtctgtgc tgactcagcc accctcagcg tctgggaccc ccgggcagag ggtcaccatc     60
tcttgttctg gaagcagctc caacatcgga actaatactg tgaactggta tcagcagctc    120
ccaggaacgg cccccaaact cctcatctat aggaattatc agagaccctc aggggtccct    180
gaccgattct ctggctccaa gtctggcacc tcagcctccc tggccatcag tgggctccgg    240
tccgaggatg aggctgatta ttactgtgca gcatgggatg atagcctgag tggtccacat    300
gtggtattcg gcggaggaac caagctgacg gtcctaggtc agcct                    345
```

<210> SEQ ID NO 47
<211> LENGTH: 345
<212> TYPE: DNA
<213> ORGANISM: Artificial Sequence
<220> FEATURE:
<223> OTHER INFORMATION: U4-4-VL

<400> SEQUENCE: 47

```
cagtctgtgc tgactcagcc accctcagcg tctgggaccc ccgggcagag ggtcaccatc     60
tcttgttctg gaagcagctc caacatcgga agtaatactg taaactggta tcagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtccccta    300
gtggtattcg gcggaggaac caagctgacg gtcctaggtc agcct                    345
```

<210> SEQ ID NO 48
<211> LENGTH: 339
<212> TYPE: DNA
<213> ORGANISM: Artificial Sequence
<220> FEATURE:
<223> OTHER INFORMATION: U4-5-VL

<400> SEQUENCE: 48

```
cagtctgtgc tgactcagcc accctcagcg tctgggaccc ccgggcagag ggtcaccatc     60
tcttgttctg gaagcagctc caacatcgga agtaatactg taaactggta tcagcagctc    120
```

```
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgttca acgtgggatg acagcctgag aggttgggtg    300
ttcggcggag gaaccaagct gacggtccta ggtcagcct                          339
```

<210> SEQ ID NO 49
<211> LENGTH: 345
<212> TYPE: DNA
<213> ORGANISM: Artificial Sequence
<220> FEATURE:
<223> OTHER INFORMATION: U4-8-VL

<400> SEQUENCE: 49

```
cagtctgtgc tgactcagcc accctcagca tctgggaccc ccgggcagag ggtcaccatc    60
tcttgttctg gaagcagctc caacatcgga agtaatactg taaactggta tcagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtccctat    300
tgggtgttcg gcggaggaac caagctgacg gtcctaggtc agcct                   345
```

<210> SEQ ID NO 50
<211> LENGTH: 339
<212> TYPE: DNA
<213> ORGANISM: Artificial Sequence
<220> FEATURE:
<223> OTHER INFORMATION: U4-6-VL

<400> SEQUENCE: 50

```
cagtctgtgc tgactcagcc accctcagcg tctgggaccc ccgggcagag ggtcaccatc    60
tcttgttctg gaagcagctc caacatcgga agtaatactg taaactggta tcagcagctc    120
ccaggaacgg cccccaaact cctcatctat tatgatgatc tgctgccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtccggtg    300
ttcggcggag gaaccaagct gacggtccta ggtcagcct                          339
```

<210> SEQ ID NO 51
<211> LENGTH: 345
<212> TYPE: DNA
<213> ORGANISM: Artificial Sequence
<220> FEATURE:
<223> OTHER INFORMATION: U4-7-VL and U4-9-VL

<400> SEQUENCE: 51

```
cagtctgtgc tgactcagcc accctcagcg tctgggaccc ccgggcagag ggtcaccatc    60
tcttgttctg gaagcagctc caacatcgga agtaatactg tacactggta tcagcagctc    120
ccaggaacgg cccccaaact cctcatctat agaaataatc ggcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggtccgaat    300
gtggtattcg gcggaggaac caagctgacg gtcctaggtc agcct                   345
```

<210> SEQ ID NO 52
<211> LENGTH: 118
<212> TYPE: PRT
<213> ORGANISM: Artificial Sequence

```
<220> FEATURE:
<223> OTHER INFORMATION: U4-1-VH

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ser Pro Gly Ala Phe Asp Ile Trp Gly Gln Gly Thr
            100                 105                 110

Leu Val Thr Val Ser Ser
        115

<210> SEQ ID NO 53
<211> LENGTH: 133
<212> TYPE: PRT
<213> ORGANISM: Artificial Sequence
<220> FEATURE:
<223> OTHER INFORMATION: U4-2-VH

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Ala
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ser Tyr Gly Asp Phe Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 54
<211> LENGTH: 133
<212> TYPE: PRT
<213> ORGANISM: Artificial Sequence
<220> FEATURE:
<223> OTHER INFORMATION: U4-3-VH and U4-9-VH

<400> SEQUENCE: 54

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Leu Thr Ala Tyr Gly His Val Asp Ser Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser
            130
```

<210> SEQ ID NO 55
<211> LENGTH: 134
<212> TYPE: PRT
<213> ORGANISM: Artificial Sequence
<220> FEATURE:
<223> OTHER INFORMATION: U4-4-VH

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Leu Ile Ser Gly Ser Gly Gly Ser Thr Tyr Tyr Ala Asp Ser Val
    50                  55                  60

Gln Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Asn Thr Ala Gly Phe Gly Tyr Phe Asp Leu Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser
            130
```

<210> SEQ ID NO 56
<211> LENGTH: 136
<212> TYPE: PRT
<213> ORGANISM: Artificial Sequence
<220> FEATURE:
<223> OTHER INFORMATION: U4-5-VH

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Asn Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Thr Lys Ser Arg Asp Phe Trp Arg Gly Pro Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser
            130                 135

<210> SEQ ID NO 57
<211> LENGTH: 133
<212> TYPE: PRT
<213> ORGANISM: Artificial Sequence
<220> FEATURE:
<223> OTHER INFORMATION: U4-8-VH

<400> SEQUENCE: 57

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
             20                  25                  30

Tyr Met Ser Trp Val Arg Gln Ala Pro Gly Lys Gly Leu Glu Trp Val
            35                  40                  45

Ser Ser Ile Ser Gly Ser Gly Gly Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Met Thr Val Phe Gly Ala Ala Thr Leu Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser
            130

<210> SEQ ID NO 58
<211> LENGTH: 131
<212> TYPE: PRT
<213> ORGANISM: Artificial Sequence
<220> FEATURE:
<223> OTHER INFORMATION: U4-6-VH

<400> SEQUENCE: 58

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Tyr Met Asn Trp Val Arg Gln Ala Pro Gly Lys Gly Leu Glu Trp Val
            35                  40                  45

Ser Ala Ile Gly Gly Ser Gly Asp Arg Thr Tyr Tyr Ala Asp Ser Val
        50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                85                  90                  95

Ala Leu Gly Gly Ser Tyr Phe Gly Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser
    130

<210> SEQ ID NO 59
<211> LENGTH: 133
<212> TYPE: PRT
<213> ORGANISM: Artificial Sequence
<220> FEATURE:
<223> OTHER INFORMATION: U4-7-VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Ala Thr Tyr Gly Pro Phe Asp Asp Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser
            130

<210> SEQ ID NO 60
<211> LENGTH: 115
<212> TYPE: PRT
<213> ORGANISM: Artificial Sequence
<220> FEATURE:
<223> OTHER INFORMATION: U4-1-VL

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Gly Thr Ser Asn Ile Gly Thr Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
            50                  55                  60

Gly Ser Lys Ser Gly Thr Ser Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95
```

Asn Gly Pro Tyr Val Val Phe Gly Gly Gly Thr Lys Leu Thr Val Leu
            100                 105                 110

Gly Gln Pro
        115

<210> SEQ ID NO 61
<211> LENGTH: 115
<212> TYPE: PRT
<213> ORGANISM: Artificial Sequence
<220> FEATURE:
<223> OTHER INFORMATION: U4-2-VL

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Ala Val Val Phe Gly Gly Gly Thr Lys Leu Thr Val Leu
            100                 105                 110

Gly Gln Pro
        115

<210> SEQ ID NO 62
<211> LENGTH: 115
<212> TYPE: PRT
<213> ORGANISM: Artificial Sequence
<220> FEATURE:
<223> OTHER INFORMATION: U4-3-VL

<400> SEQUENCE: 62

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro His Val Val Phe Gly Gly Gly Thr Lys Leu Thr Val Leu
            100                 105                 110

Gly Gln Pro
        115

<210> SEQ ID NO 63
<211> LENGTH: 115
<212> TYPE: PRT
<213> ORGANISM: Artificial Sequence

```
<220> FEATURE:
<223> OTHER INFORMATION: U4-4-VL

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Leu Val Val Phe Gly Gly Gly Thr Lys Leu Thr Val Leu
            100                 105                 110

Gly Gln Pro
        115

<210> SEQ ID NO 64
<211> LENGTH: 113
<212> TYPE: PRT
<213> ORGANISM: Artificial Sequence
<220> FEATURE:
<223> OTHER INFORMATION: U4-5-VL

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Thr Trp Asp Asp Ser Leu
                85                  90                  95

Arg Gly Trp Val Phe Gly Gly Gly Thr Lys Leu Thr Val Leu Gly Gln
            100                 105                 110

Pro

<210> SEQ ID NO 65
<211> LENGTH: 115
<212> TYPE: PRT
<213> ORGANISM: Artificial Sequence
<220> FEATURE:
<223> OTHER INFORMATION: U4-8-VL

<400> SEQUENCE: 65

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
```

```
              35                  40                  45

Ile Tyr Arg Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Tyr Trp Val Phe Gly Gly Gly Thr Lys Leu Thr Val Leu
            100                 105                 110

Gly Gln Pro
        115

<210> SEQ ID NO 66
<211> LENGTH: 113
<212> TYPE: PRT
<213> ORGANISM: Artificial Sequence
<220> FEATURE:
<223> OTHER INFORMATION: U4-6-VL

<400> SEQUENCE: 66

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Tyr Asp Asp Leu Leu Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu Gly Gln
            100                 105                 110

Pro

<210> SEQ ID NO 67
<211> LENGTH: 115
<212> TYPE: PRT
<213> ORGANISM: Artificial Sequence
<220> FEATURE:
<223> OTHER INFORMATION: U4-7-VL and U4-9-VL

<400> SEQUENCE: 67

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val His Trp Tyr Gln Gln Leu Pro Gly Thr Ala Pro Lys Leu Leu
         35                  40                  45

Ile Tyr Arg Asn Asn Arg Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Pro Asn Val Val Phe Gly Gly Gly Thr Lys Leu Thr Val Leu
```

```
                         100                 105                 110

Gly Gln Pro
        115

<210> SEQ ID NO 68
<211> LENGTH: 13
<212> TYPE: PRT
<213> ORGANISM: Artificial Sequence
<220> FEATURE:
<223> OTHER INFORMATION: U4-7 and U4-9 CDRL1

<400> SEQUENCE: 68

Ser Gly Ser Ser Ser Asn Ile Gly Ser Asn Thr Val His
1               5                   10

<210> SEQ ID NO 69
<211> LENGTH: 4
<212> TYPE: PRT
<213> ORGANISM: Artificial Sequence
<220> FEATURE:
<223> OTHER INFORMATION: epitope

<400> SEQUENCE: 69

Arg Tyr Asn Tyr
1

<210> SEQ ID NO 70
<211> LENGTH: 802
<212> TYPE: PRT
<213> ORGANISM: Artificial Sequence
<220> FEATURE:
<223> OTHER INFORMATION: FGFR4

<400> SEQUENCE: 70

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Thr Pro Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205
```

```
Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
                260                 265                 270

Val Tyr Ser Asp Ala Gln Pro His Ile Gln Trp Leu Lys His Ile Val
            275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
                340                 345                 350

Glu Glu Asp Pro Thr Trp Thr Ala Ala Ala Pro Glu Ala Arg Tyr Thr
            355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
            435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
    610                 615                 620
```

```
Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr
```